(12) United States Patent
Hanf

(10) Patent No.: US 11,857,523 B2
(45) Date of Patent: *Jan. 2, 2024

(54) METHODS OF TREATMENT OF CHOLESTATIC DISEASES

(71) Applicant: Genfit, Loos (FR)

(72) Inventor: Remy Hanf, Lille (FR)

(73) Assignee: Genfit, Loos (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/212,029

(22) Filed: Jun. 20, 2023

(65) Prior Publication Data

US 2023/0338312 A1 Oct. 26, 2023

Related U.S. Application Data

(63) Continuation of application No. 17/533,767, filed on Nov. 23, 2021, which is a continuation of application No. 16/894,110, filed on Jun. 5, 2020, now Pat. No. 11,331,292, and a continuation-in-part of application No. 16/090,415, filed as application No. PCT/EP2017/057634 on Mar. 30, 2017, now Pat. No. 11,185,519.

(30) Foreign Application Priority Data

Mar. 31, 2016 (EP) ..................... 16305381

(51) Int. Cl.
*A61K 31/192* (2006.01)
*A61P 37/06* (2006.01)
*A61K 45/06* (2006.01)

(52) U.S. Cl.
CPC ............ *A61K 31/192* (2013.01); *A61K 45/06* (2013.01); *A61P 37/06* (2018.01)

(58) Field of Classification Search
CPC .............................. A61K 31/192; A61P 37/06
See application file for complete search history.

(56) References Cited

U.S. PATENT DOCUMENTS

| 8,772,342 B2 | 7/2014 | Darteil et al. |
| 11,185,519 B2 * | 11/2021 | Hanf .................. A61P 1/16 |
| 11,331,292 B2 * | 5/2022 | Hanf .................. A61P 1/16 |
| 2007/0197606 A1 | 8/2007 | Burczynski et al. |

FOREIGN PATENT DOCUMENTS

| WO | WO-2016/127019 A2 | 8/2016 |
| WO | 2017/167935 A1 | 10/2017 |
| WO | 2018/060372 A1 | 4/2018 |
| WO | 2019/053582 A1 | 3/2019 |
| WO | 2019/067373 A1 | 4/2019 |

OTHER PUBLICATIONS

Hegade et al. Clinical Medicine, 2015, vol. 15, No. 4, p. 351-357 (Year: 2015).*
Hegade et al. Frontline Gastroenterology, 2016, vol. 7, p. 158-166 (Published Online Aug. 26, 2015) (Year: 2016).*
Cariou et al "Effects of the New Dual PPARa/o Agonist GFT505 on Lipid and Glucose Homeostasis in Abdominally Obese Patients with Combined Dyslipidemia or Impaired Glucose Metabolism" Diabetes Care vol. 34, pp. 2008-2014, 2011.
Cariou et al "GFT505 for the Treatment of Nonalcoholic Steatohepatitis and Type 2 Diabetes" Expert Opinion on Investigational Drugs vol. 23, pp. 1441-1448, 2014.
Dohmen et al "The Effectiveness of Fenofibrate in Comparison to Bezafibrate for Patients with Asymptomatic Primary Biliary Cirrhosis" Fukuoka Acta Medica vol. 104, pp. 350-361, 2013.
El-Sisi et al "Effects of Three Different Fibrates on Intrahepatic Cholestasis Experimentally Induced in Rats" PPAR Research vol. 2013, pp. 1-10, 2013.
Ghonem et al "Fibrates and Cholestasis" Hepatology vol. 62, pp. 635-643, 2015.
Halilbasic et al "Nuclear Receptors as Drug Targets in Cholestatic Liver Diseases" Clinical Liver Disease vol. 17, pp. 161-189, 2013.
Marra et al "Thiazolidinedione Treatment Inhibits Bile Duct Proliferation and Fibrosis in a Rat Model of Chronic Cholestasis" World Journal of Gastroenterology vol. 11, pp. 4931-4938, 2005.
Nicolopoulos et al "Chronic Anicteric Intrahepatic Cholestasis Associated with Ankylosing Spondylitis. Beneficial Treatment by Clofibrate" Digestion vol. 24, pp. 69-72, 1982.
Staels et al "Hepatoprotective Effects of the Dual Peroxisome Proliferator-Activated Receptor Alpha/Delta Agonist, GFT505, in Rodent Models of Nonalcoholic Fatty Liver Disease/Nonalcoholic Steatohepatitis" Hepatology vol. 58, pp. 1941-1952, 2013.
Khanna, et al., "Novel strategies and therapeutic options for the management of primary biliary cholangitis," Therapeutic Advances in Gastroenterology, vol. 10(10), pp. 791-803, 2017.
Liu, et al., "Early investigational drugs targeting PPAR-a for the treatment of metabolic disease," Expert Opinion on Investigational Drugs, vol. 24(5); 2015.
Genfit, "FDA and EMA Grant GENFIT's Elafibranor Orphan Drug Designation for Primary Biliary Cholangitis (PBC)," Retrieved online on Jul. 13, 2020.
Ostadhadi, et al., "The role of PPAR-gamma receptor in pruritus," European Journal of Pharmacology, 762, pp. 322-325, 2015.
Benedetta, et al., "The challenges of primary biliary cholangitis: What is new and what needs to be done," Journal of Autoimmunity, 105, 2019.
Galoosian, et al, "Clinical Updates in Primary Biliary Cholangitis: Trends, Epidemiology, Diagnostics, and New Therapeutic Approaches," Journal of Clinical and Translational Hepatology vol. 8, pp. 49-60, Jan. 29, 2020.
Hegade, et al., "Novel Bile Acid Therapeutics for the Treatment of Chronic Liver Diseases," Therapeutic Advances in Gastroenterology vol. 9, pp. 376-391, 2015.
Krones, et al., "Future Medical Treatment of PSC," Current Hepatology Reports vol. 18, pp. 96-106, Feb. 13, 2019.

(Continued)

*Primary Examiner* — James D. Anderson
(74) *Attorney, Agent, or Firm* — Morse, Barnes-Brown & Pendleton, P.C.; Martin Z. Zhang, Esq.

(57) ABSTRACT

The present invention relates to the use of compound 1-[4-methylthiophenyl]-3-[3,5-dimethyl-4-carboxydimethylmethyloxyphenyl]prop-2-en-1-one (Elafibranor or GFT505) for treating cholestatic diseases, and more specifically PBC and/or PSC.

9 Claims, 8 Drawing Sheets

(56) References Cited

OTHER PUBLICATIONS

Figure 1:
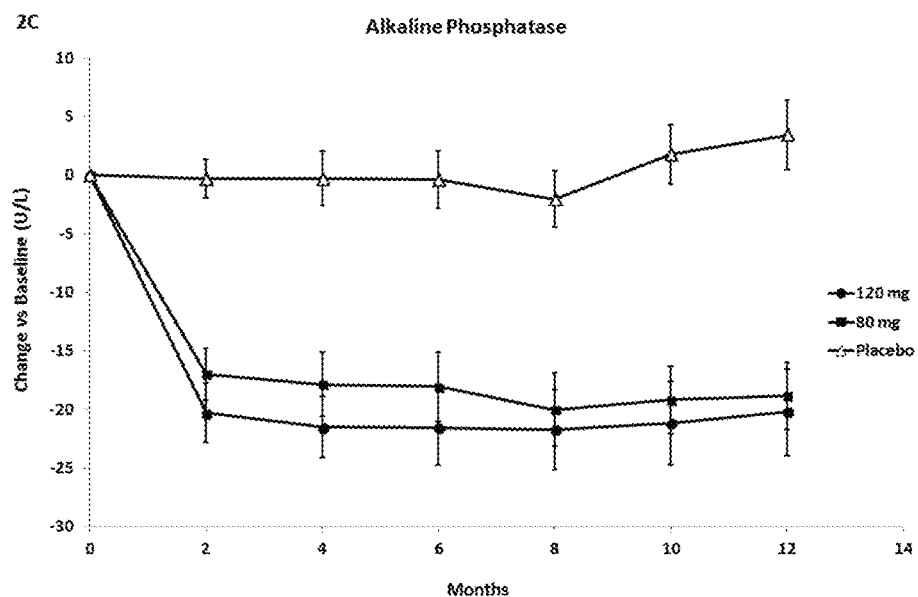

Ratziu, et al., "Novel Pharmacotherapy Options for NASH," Digestive Diseases and Sciences vol. 61, pp. 1398-1405, Mar. 22, 2016.
Chascsa, et al., "Emerging therapies for PBC," J Gastroenterol, 55(3): 261-272, 2020.
Baschet, et al., "Cost-Effectiveness Analysis of Obeticholic Acid For The Treatment of Primary Biliary Cholangitis (PBC) Patients With Inadequate Response or Intolerance To Ursodeoxycholic Acid (UDCA) In France," Value in Health, vol. 20(9), 2017.

\* cited by examiner

METHODS OF TREATMENT OF CHOLESTATIC DISEASES

CROSS-REFERENCE TO RELATED APPLICATIONS

This application is a continuation of U.S. patent application Ser. No. 17/533,767, filed Nov. 23, 2021, which is a continuation of U.S. patent application Ser. No. 16/894,110, filed Jun. 5, 2020, and a continuation-in-part of U.S. patent application Ser. No. 16/090,415, filed Oct. 1, 2018, which is the national stage of International Application No. PCT/EP2017/057634, filed Mar. 30, 2017, which claims the benefit of European Application No. 16305381.2, filed Mar. 31, 2016. The entire disclosure of each application is hereby incorporated by reference.

TECHNICAL FIELD

The present invention relates to the field of medicine, in particular the treatment of cholestatic diseases, and more specifically PBC and/or PSC.

BACKGROUND

The present invention is dedicated to cholestasis or cholestatic diseases, also mainly characterized by two distinct pathologies: PBC (Primary Biliary Cholangitis, previously named Primary Biliary Cirrhosis (Beuers et al, 2015)) and/or PSC (Primary Sclerosing Cholangitis).

Cells in the liver produce bile, which passes through ducts within the liver to the gallbladder. Bile is a digestive liquid that is made in the liver. It travels through the bile ducts to the gallbladder and the small intestine, where it helps digest fats and fatty vitamins.

Cholestasis is a condition that results from an impairment of bile formation or bile flow to the gallbladder and duodenum (first section of the small intestine). The effects of cholestasis are profound and widespread, leading to worsening liver disease and systemic illness, liver failure, and the need for liver transplantation.

Cholestasis may be classified as intrahepatic or extrahepatic. Intrahepatic cholestasis primarily involves the bile canaliculi and the intrahepatic bile ducts. Extrahepatic cholestasis involves the extrahepatic ducts, the common hepatic duct or the common bile duct.

Primary Biliary Cholangitis, or PBC, is a chronic inflammatory intrahepatic, or long-term, liver disorder that slowly destroys the small-to-medium-sized bile ducts (tube-like structures that carry bile) within the liver. In patients with PBC, the bile ducts are destroyed by inflammation. This causes bile to remain in the liver, where gradual injury damages liver cells and causes cirrhosis, or scarring of the liver.

PBC is considered as a rare disease, with a prevalence of 40 cases per 100000. The diagnosis of PBC is typically established between the ages of 30 and 60 years. PBC develops in all races, and 90% of cases occur in women. The disease accounts for 2 to 3% of deaths due to cirrhosis (Boonstra et al, 2012; Zetterman, 2015).

Primary Biliary Cholangitis (PBC) was previously named Primary Biliary Cirrhosis, but health officials from around the world have overwhelmingly supported changing the name of Primary Biliary Cirrhosis to Primary Biliary Cholangitis. Since cirrhosis occurs only in the late stage, the name primary biliary cirrhosis is actually a misnomer for patients in the earlier stages of the illness. Changing the name to primary biliary cholangitis will better serve patients and the medical community worldwide (Beuers et al, 2015).

Although genetic or environmental factors are associated with the risk of PBC, the causes are still unknown, and most experts consider PBC as an autoimmune disease.

PBC advances slowly. Many patients lead active and productive lives for more than 10 to 15 years after diagnosis. Patients who show no symptoms at the time of diagnosis often remain symptom-free for years. Patients who have normal liver tests on treatment may have a normal life expectancy. PBC is a chronic illness and may lead to life-threatening complications, especially after cirrhosis develops.

The first signs being a generalized fatigue (in 70% of cases) and the appearance of pruritus and itching. However, most of the patients are asymptomatic in the early stage of the disease. The diagnosis is established by standard biomedical analyses including the measurement of anti-mitochondrial antibodies (AMAs, which reflect the autoimmune character), and liver enzymes such as alkaline phosphatase.

Ursodeoxycholic acid (UDCA) and Obeticholic acid (OCA) are the only therapies approved by the FDA for the treatment of PBC (Purohit & Cappell, 2015). UDCA is the first line therapy for PBC but is efficient in only 60% of patients. The other 40% respond weakly or not at all to the treatment, and are therefore at high risk of developing cirrhosis, liver insufficiency, and ultimately requiring a liver transplantation.

Primary Sclerosing Cholangitis (PSC) is a chronic, or long-term, disease that slowly damages the extra- and intrahepatic bile ducts. In patients with PBC, the bile ducts are destroyed by inflammation, and in patients with PSC, they become blocked due to inflammation and deteriorating. In both cases, this causes bile to accumulate in the liver, where it gradually damages liver cells and causes cirrhosis, or damage of the liver.

As described for PBC, the cause is still unknown but the immune system is believed to play a major role. About 70 percent of patients are men. It may be related to bacterial or viral infections, as well as problems in the immune system. Genetic factors may also play a role. PSC is considered an uncommon disease, but recent studies suggest that it may be more common than previously thought. This disease is often associated with inflammatory diseases of the intestine such as hemorrhagic rectocolitis, and accounts for 40% of liver abnormalities related with this disease.

It is a rare disease that affects predominantly men (70% of the patients) with an estimated prevalence of 1 to 5 cases per 10 000 persons.

PSC advances very slowly. Many patients may have the disease for years before symptoms develop. Symptoms may remain at a stable level, they may come and go, or they may progress gradually. Liver failure may occur 10-15 years after diagnosis, but this may take even longer for some PSC patients. Many people with PSC will ultimately need a liver transplant, typically about 10 years after being diagnosed with the disease. PSC may also lead to bile duct cancer. Endoscopy and MRI tests may be done to monitor the disease.

Many people with PSC do not get symptoms, especially in the early stages of the disease. When symptoms do occur the most common are fatigue, pruritus, or itching of the skin, and jaundice, a yellowing of the skin and eyes. These symptoms may come and go, but they may worsen over time. As the disease continues, the bile ducts may become infected, which can lead to episodes of fever, chills and abdominal pain.

Because many PSC patients have no symptoms, the disease is often discovered through abnormal results on routine liver blood tests. The diagnosis will be completed based on a combination of biochemical, histological and imaging analyses. Formal diagnosis is usually made by cholangiography, an X-ray test involving injection of dye into the bile ducts, or by an MRI.

Although UDCA treatment may be beneficial for some patients, there is currently no therapy that significantly reduces the risk of death or the need for liver transplantation, which still remains the only solution for patient survival.

The need for novel therapeutic options for the management of cholestatic diseases, in particular PSC and/or PBC, is still clear and urgent.

Elafibranor is being developed by Genfit for the treatment of non-alcoholic steatohepatitis. The present inventors herein show that the profile of Elafibranor also makes it a therapeutic asset for the treatment of PBC.

SUMMARY OF INVENTION

A clinical study has surprisingly shown that the treatment of patients with 1-[4-methylthiophenyl]-3-[3,5-dimethyl-4-carboxydimethylmethyloxyphenyl]prop-2-en-1-one (Elafibranor, formerly called GFT505) provides a relevant reduction of biochemical markers in the plasma, demonstrating that this compound is advantageous for the treatment of cholestatic diseases.

The present invention relates to elafibranor for use for the treatment of a cholestatic disease.

The present invention also provides the use of elafibranor in the preparation of a pharmaceutical composition for treating a cholestatic disease.

In a further embodiment, the present invention also discloses the use of elafibranor in the manufacture of a medicament for treating a cholestatic disease.

The present invention further relates to a method for treating a cholestatic disease in a subject in need thereof, comprising administering a therapeutic effective amount of elafibranor, in particular thereby inducing a reduction in cholestasis.

In a particular embodiment of the invention, elafibranor is administered at a dose varying between 0.01 mg and 1 g per administration, preferentially from 1 mg to 150 mg per administration, and more preferably from 70 mg to 130 mg. In a particular embodiment, elafibranor is administered once a day. In another particular embodiment, elafibranor is administered once a day at a dose of 80 or 120 mg The invention also provides a pharmaceutical composition comprising compound elafibranor for use for treating a cholestatic disease.

According to the invention, the pharmaceutical composition may be formulated in the form of injectable suspensions, gels, oils, pills, tablets, suppositories, powders, gel caps, capsules, aerosols or means of galenic forms or devices assuring a prolonged and/or slow release.

In particular, the pharmaceutical composition comprises compound elafibranor and a pharmaceutically acceptable carrier and/or excipient.

In another embodiment of the invention, the invention also discloses a kit for treating a cholestatic disease or for use for treating a cholestatic disease, the kit comprising elafibranor.

According to the present invention, the disclosed method, compound, uses, composition or kit concern the treatment of a cholestatic disease preferably selected in the group consisting in Primary Biliary Cholangitis, Primary Sclerosing Cholangitis, Intrahepatic Cholestasis of Pregnancy, Progressive Familial Intrahepatic Cholestasis, Biliary atresia, Cholelithiasis, Infectious Cholangitis, Cholangitis associated with Langerhans cell histiocytosis, Alagille syndrome, Nonsyndromic ductal paucity, Drug-induced cholestasis, and Total parenteral nutrition-associated cholestasis.

In a preferred embodiment, the cholestatic disease is PBC or PSC.

In another preferred embodiment, the cholestatic disease is PBC.

DESCRIPTION OF THE FIGURES AND TABLES

Abbreviations used in the figures, in the tables, and in the text:

| | |
|---|---|
| AE | adverse event |
| ALP | Alkaline Phosphatase |
| ALT | Alanine Transaminase |
| AMA | anti-mitochondrial antibody |
| ASBTi | apical sodium-codependent bile acid transporter inhibitors |
| AST | Aspartate Aminotransferase |
| BCL6 | B-cell lymphoma 6 |
| C4 | serum 7α-hydroxy-4-cholesten-3-one |
| CDCA | chenodeoxycholic acid |
| CK-18 | cytokeratine-18 |
| CPK | creatine phosphokinase |
| DCA | deoxycholic acid |
| ECG | electrocardiogram |
| eGFR | estimated glomerular filtration rate |
| FDA | Food and Drug Administration |
| FGF19 | Fibroblast growth factor 19 |
| FXR | Farnesoid X receptor |
| γGT | gamma-Glutamyl-Transferase |
| HBV | hepatitis B virus |
| HCB | hepatitis C virus |
| HDL-C | High Density Lipoprotein-Cholesterol |
| HIV | human immunodeficiency virus |
| IC | informed consent |
| ICP | Intrahepatic Cholestasis of Pregnancy |
| IgM | immunoglobulin M |
| IL-6 | interleukin-6 |
| IRB | institutional review board |
| ITT | Intention To Treat |
| IVRS | interactive voice response system |
| IWRS | interactive web response system |
| LDL-C | Low Density Lipoprotein-Cholesterol |
| MELD | Model for End Stage Liver Disease |
| MRI | Magnetic resonance imaging |
| NASH | nonalcoholic steatohepatitis |
| NF-κB | nuclear factor kappa B |
| NOX | NADPH oxidase |
| OCA | obeticholic acid |
| PBC | Primary Biliary Chlolangitis |
| PFIC | Progressive Familial Intrahepatic Cholestasis |
| PK | pharmacokinetics |
| PPAR | Peroxisome proliferator-activated receptor |
| PSC | Primary Sclerosing Cholangitis |
| QOL | quality of life |
| TG | TriGlyceride |
| TGF-β | transforming growth factor beta |
| TIPS | transjugular intrahepatic portosystemic shunts |
| TNF-α | tumor necrosis factor alpha |
| TPN | Total parenteral nutrition |
| UDCA | ursodeoxycholic acid |
| ULN | upper limit of normal |
| VAS | visual analogue score |

FIG. 1: Dosage of Alkaline Phosphatase

NASH patients treated with both elafibranor doses (80 mg and 120 mg) improved alkaline phosphatase levels compared to placebo group. FIG. 1 shows changes from baseline in liver enzyme in treatment groups of the efficacy evaluable set (n=237). Results are expressed in mean values of changes from baseline during treatment with placebo (n=77), elafibranor 80 mg (n=82) and elafibranor 120 mg (n=78). Error bars represent 95% CIs.

Figure 2:
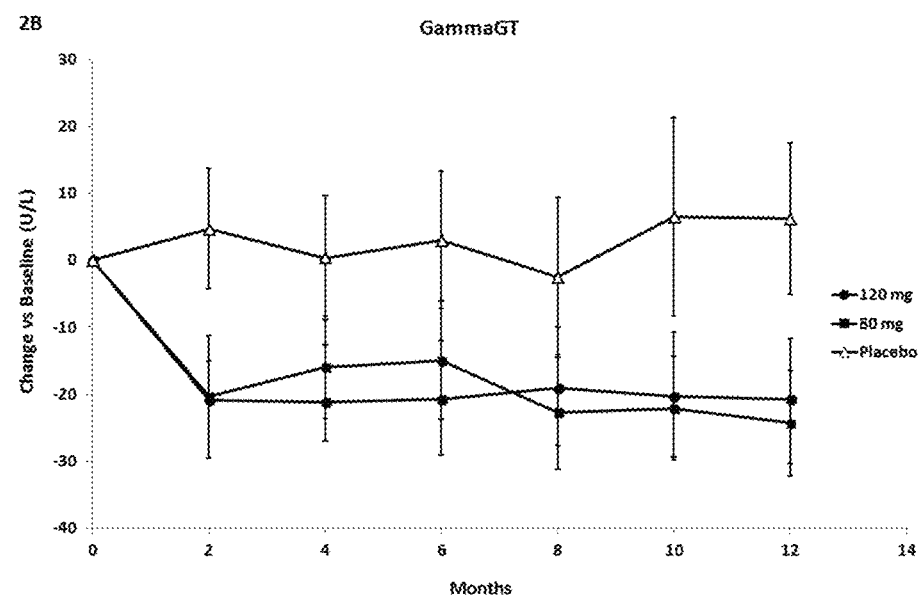

FIG. 2: Dosage of γGT

NASH patients treated with both elafibranor doses (80 mg and 120 mg) improved γGT levels compared to placebo group. FIG. 2 shows changes from baseline in liver enzyme in treatment groups of the efficacy evaluable set (n=237). Results are expressed in mean values of changes from baseline during treatment with placebo (n=77), elafibranor 80 mg (n=82) and elafibranor 120 mg (n=78). Error bars represent 95% CIs.

Figure 3A:
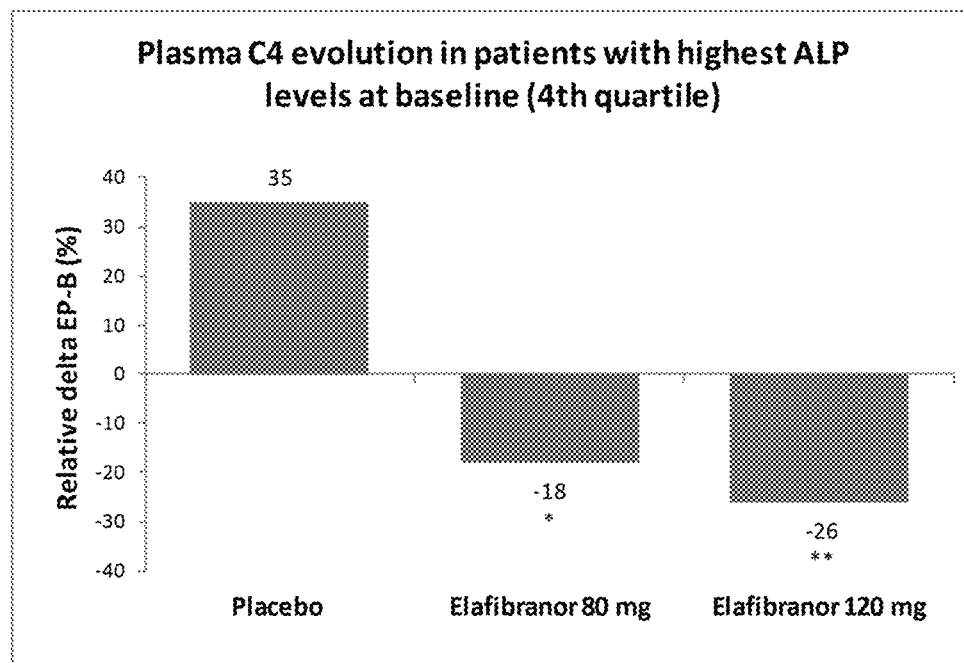
Figure 3B:
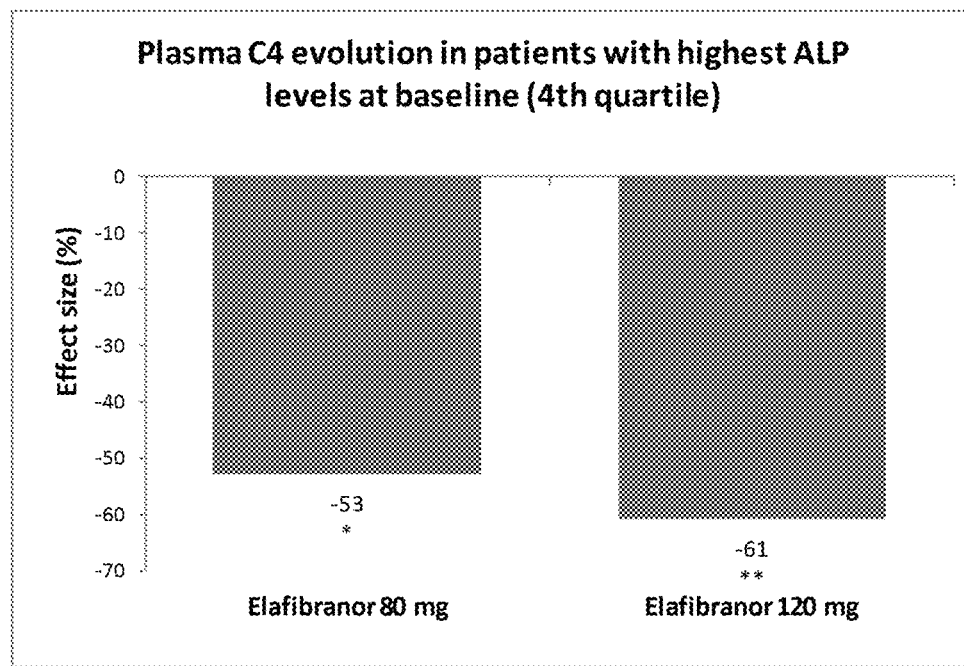

FIGS. 3A-B: Dosage of C4

FIG. 3A: NASH patients treated with both elafibranor doses (80 mg and 120 mg) improved C4 levels compared to placebo group. FIG. 3A shows changes from baseline in treatment groups of the efficacy evaluable set (n=62). Results are expressed in mean values of changes from baseline during treatment with placebo (n=23), elafibranor 80 mg (n=16) and elafibranor 120 mg (n=23).

FIG. 3B: Patients treated with both elafibranor doses (80 mg and 120 mg) improved C4 levels reported to placebo. FIG. 3B shows changes from placebo group to treatment groups of the efficacy evaluable set (n=62). Results are expressed in mean values of changes from baseline during treatment with placebo (n=23), elafibranor 80 mg (n=16) and elafibranor 120 mg (n=23).

Figure 4A:
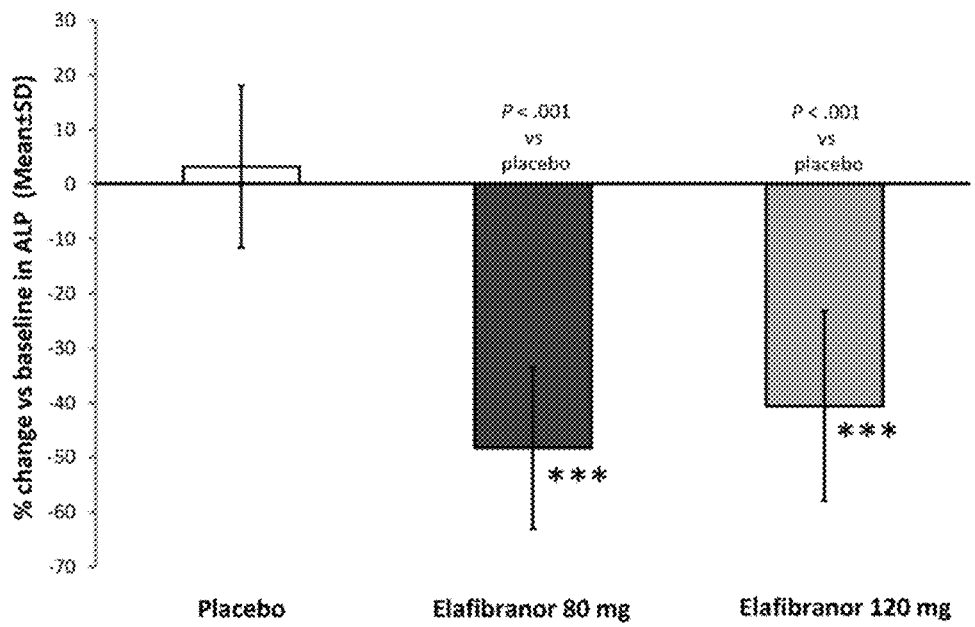
Figure 4B:
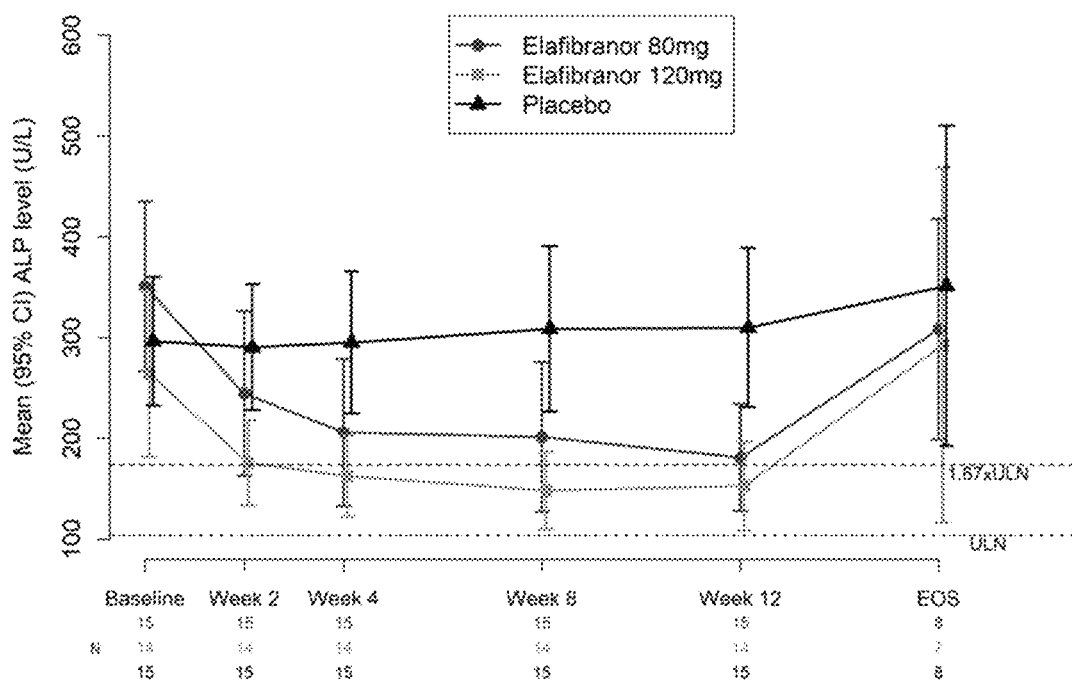
Figure 4C:
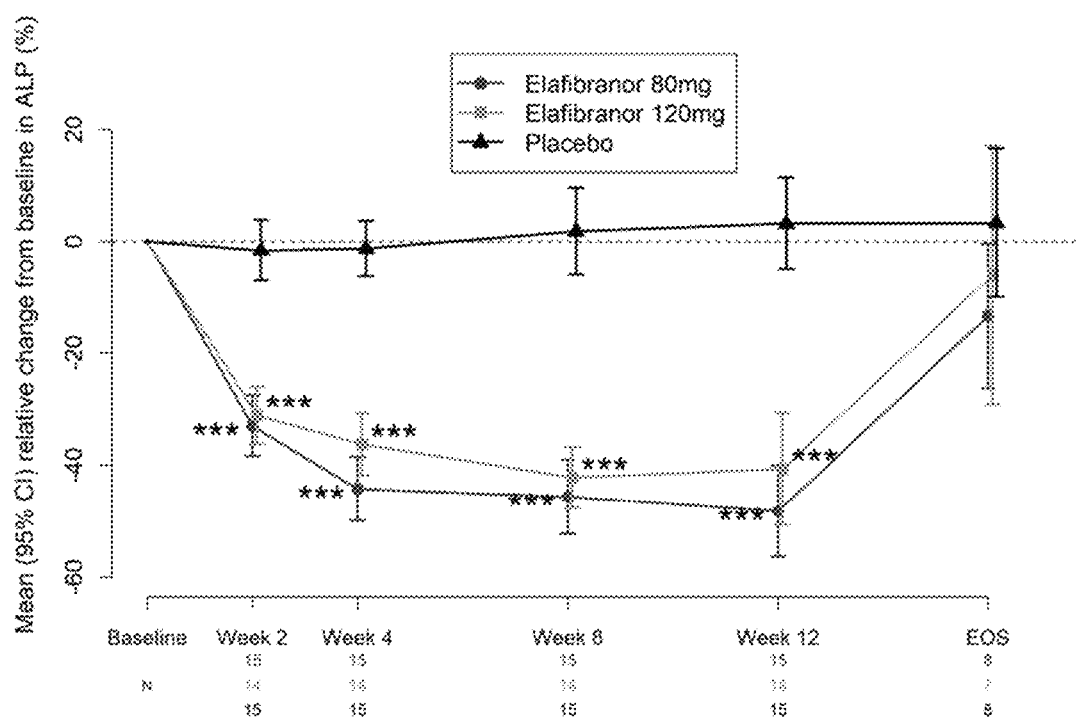

FIGS. 4A-C: Elafibranor-induced changes in ALP levels

FIG. 4A: Primary efficacy endpoint: relative percent change in ALP levels from day 0 to the end-of-treatment period (Week 12) in placebo and elafibranor-treated groups (mean±SD).

FIG. 4B: Time course of ALP levels in placebo and elafibranor-treated groups (mean±95% CI). An end-of-study (EOS) visit was planned according to a protocol amendment implemented after the study start and was performed only in a subset of patients after an off-study drug period of 16 to 30 days.

FIG. 4C: Time course of relative change vs baseline in placebo and elafibranor-treated groups (mean±95% CI). ***P<0.001 vs placebo according to non-parametric ANCOVA with baseline value as covariate. EOS is as described above for FIG. 4B.

Figure 5A:
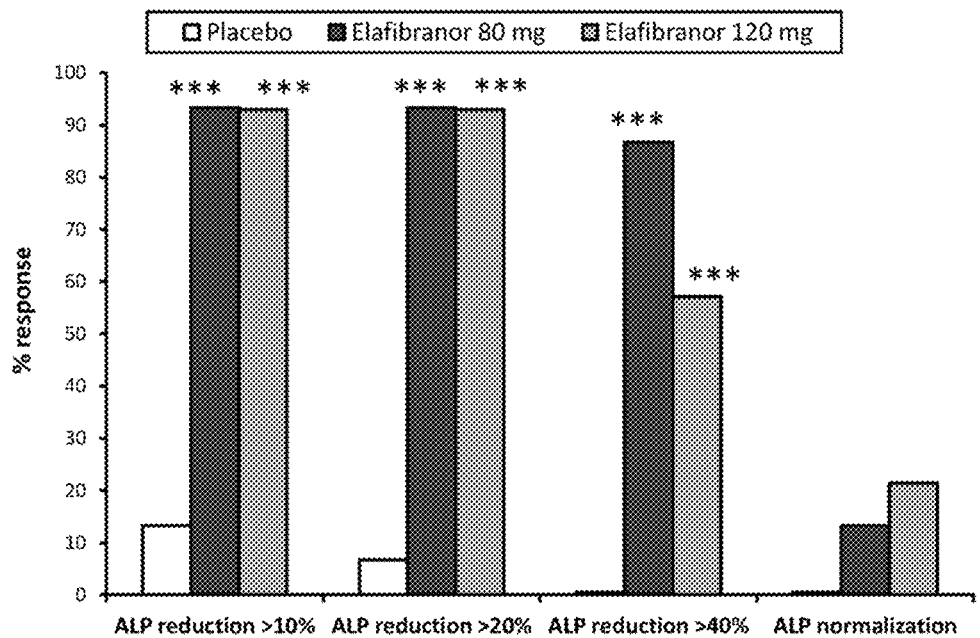
Figure 5B:
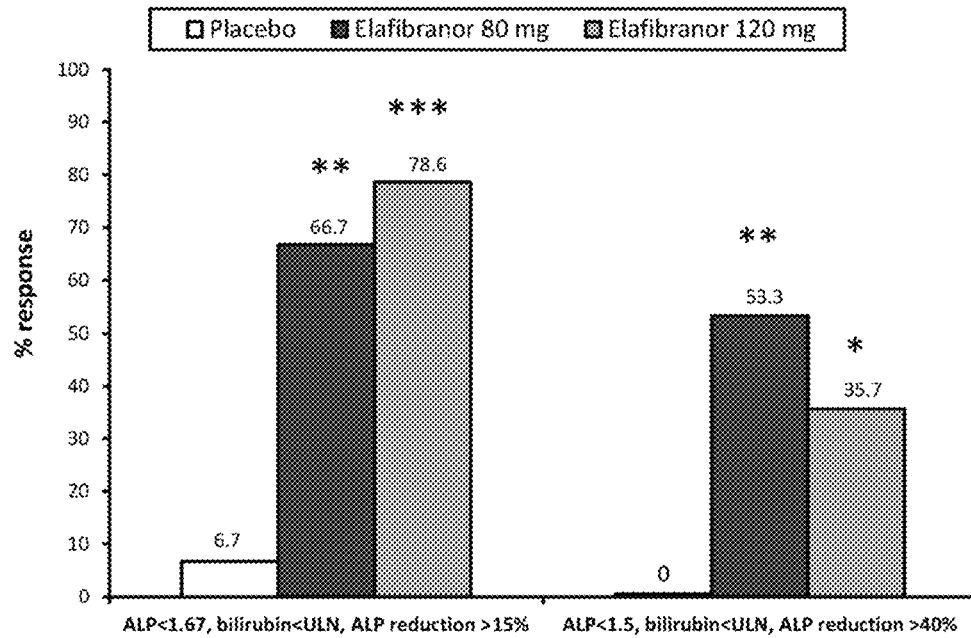

FIGS. 5A-B: Response rate

FIG. 5A: Response rate in placebo and elafibranor-treated groups of the mITT population on predefined ALP reduction objectives. Comparison of proportion of patients with a 10%, 20%, 40% reduction or ALP normalization for elafibranor dose groups with placebo group using the Fisher exact test. ***P<0.001.

FIG. 5B: Composite end-points proposed as surrogate of liver outcomes and death. Comparison with placebo group using the Fisher exact test. *P<.05; P<0.01; *P<0.001

FIGS. 6A-D: Elafibranor-induced changes in serum levels of inflammation markers

Figure 6A:
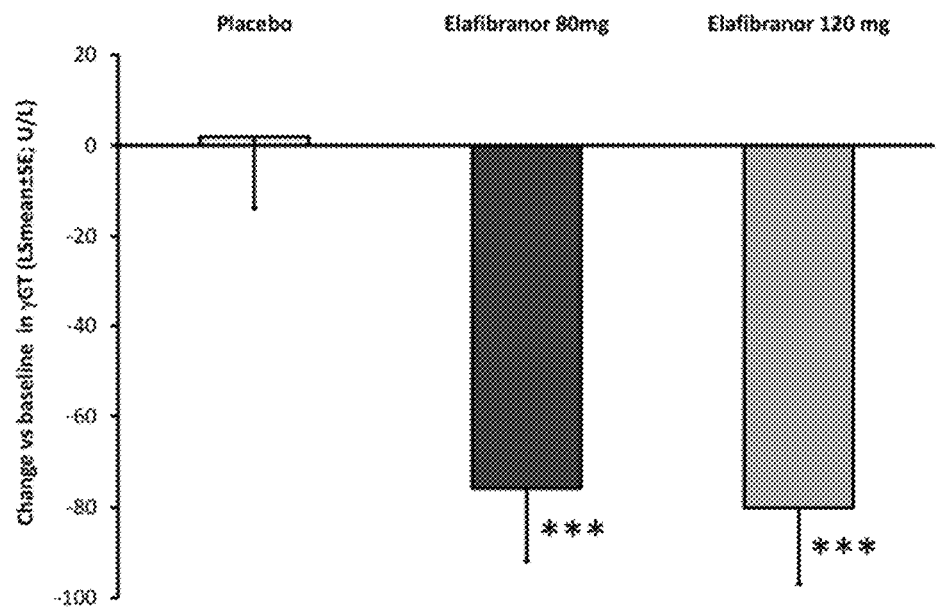

FIG. 6A: Absolute changes in γGT and levels from day 0 to the end of treatment period (Week 12) in placebo and elafibranor-treated groups (mean±SE) relative to baseline levels. ***P<0.001 vs. placebo according to ANCOVA with baseline value as covariate.

Figure 6B:
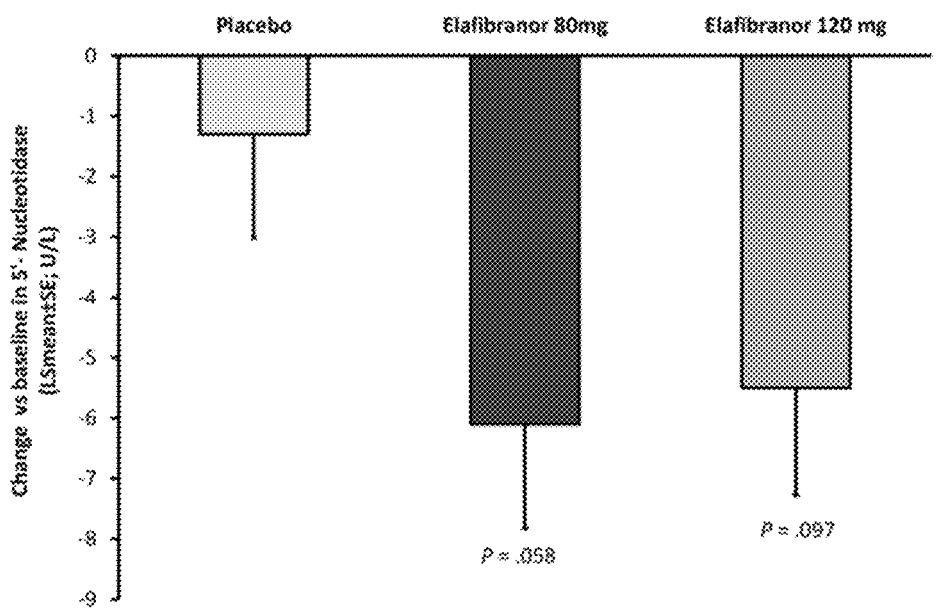

FIG. 6B: Absolute changes in 5'-nucleotidase serum levels from day 0 to the end of treatment period (Week 12) in placebo and elafibranor-treated groups (mean±SE) relative to baseline levels. P values vs. placebo according to ANCOVA with baseline value as covariate.

Figure 6C:
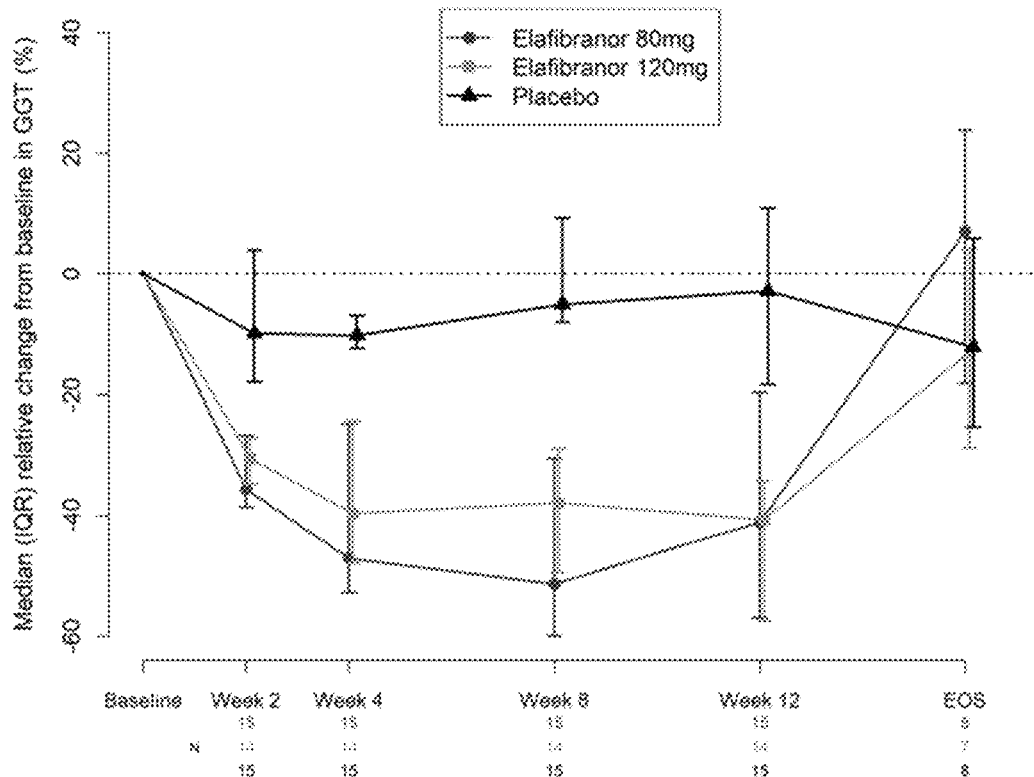

FIG. 6C: Time course of median relative changes vs. baseline in γGT serum levels in placebo and elafibranor-treated groups (median±IQR). An end-of-study (EOS) visit was planned according to a protocol amendment implemented after the study start and was performed only in a subset of patients after an off-study drug period of 16 to 30 days.

Figure 6D:
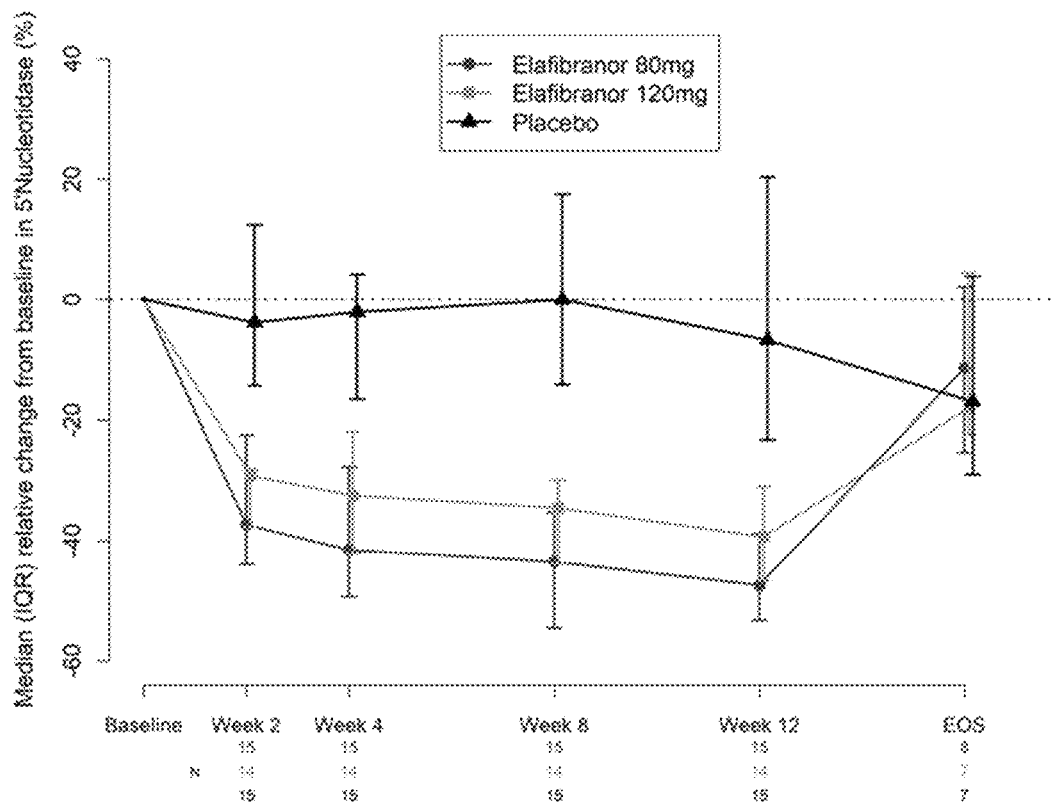

FIG. 6D: Time course of median relative changes vs. baseline in 5'-nucleotidase serum levels in placebo and elafibranor-treated groups (mediantIQR). EOS is as described above for FIG. 6C.

DETAILED DESCRIPTION OF THE INVENTION

Cholestasis or cholestatic disease is defined as a decrease in bile flow due to impaired secretion by hepatocytes (hepato-cellular cholestasis) or to obstruction of bile flow through intra- or extrahepatic bile ducts (obstructive cholestasis). In clinical practice, cholestasis is any condition in which the flow of bile from the liver is slowed or blocked.

Examples of cholestatic diseases are Primary Biliary Cholangitis (PBC) (formerly named Primary Biliary Cirrhosis), Primary Sclerosing Cholangitis (PSC), Intrahepatic Cholestasis of Pregnancy (ICP), Progressive Familial Intrahepatic Cholestasis (PFIC), Biliary atresia, Cholelithiasis, Infectious Cholangitis, Cholangitis associated with Langerhans cell histiocytosis, Alagille syndrome, Nonsyndromic ductal paucity, Drug-induced cholestasis, Total parenteral nutrition (TPN)-associated cholestasis.

In a particular embodiment, the subject to be treated has PBC. PBC is characterized by changes in many blood biochemical parameters. Patients' sera show the enhanced activity of alkaline phosphatase (ALP), γ-glutamyltransferase (gamma glutamyltranspeptidase, γGT), 5'-nucleotidase (5'-NT), and leucineaminopeptidase (LAP), the higher levels of bile acids, cholesterol, phospholipids, copper, γ-globulins, and bilirubin, and the lower level of total protein mainly at the expense of albumin fractions. In PBC, there is a decline in the levels of bile acids, cholesterol, and lecithin in the hepatic bile portion and their simultaneous rises in hepatocytes and blood (Reshetnyak, 2015). Changes in bile acid precursor C4 (7α-hydroxy-4-cholesten-3-one) (C4) can be assessed to characterize PBC.

In a particular embodiment, the patient has PBC and responds at least partly to UDCA. In another embodiment, the patient has PBC and does not respond adequately to UDCA. In a particular embodiment, elafibranor is administered, preferably orally, to a patient with PBC and inadequate response to UDCA, in particular at a dose of 80 or 120 mg.

The term "an effective amount" or "therapeutic effective amount" refers to an amount of the compound sufficient to produce the desired therapeutic result and elafibranor is administered in amounts that are sufficient to display the desired effect. In a particular aspect, the desired effect is an improvement in alkaline phosphatase and/or γGT levels signing a reduction in cholestasis. Accordingly, the invention also relates to elafibranor for use in the improvement of ALP and/or γGT levels in a subject in need thereof. In particular, elafibranor is administered for lowering the activity of ALP and/or γGT.

In a particular embodiment, elafibranor is administered to a subject with PBC for normalizing ALP, albumin and/or bilirubin level(s).

In a particular embodiment, the subject is with PBC and the treatment results in a level of ALP lower than 1.67×ULN (upper limit of normal) and total bilirubin within normal limit. The reference range of total bilirubin is 0.2-1.2 mg/dL. The reference range of direct bilirubin is 0.1-0.4 mg/dL. In a particular variant of this embodiment, elafibranor is administered for decreasing ALP level by at least 15%.

In another embodiment, the subject is with PBC and the treatment results in a level of ALP lower than 2×ULN (upper limit of normal) and total bilirubin within normal limit. In a particular variant of this embodiment, elafibranor is administered for decreasing ALP level by at least 40%.

In another particular embodiment, the subject is with PBC and the treatment results in a level of ALP lower than 1.5×ULN, total bilirubin within normal limit and a decrease of ALP level greater than 40%.

In a particular embodiment, elafibranor is administered to a subject with PBC, to improve bile acids level such as CDCA, cholic acid, litocholic acid and DCA levels.

In a further embodiment, elafibranor is administered for improving Paris I, Paris II, Toronto I, Toronto II or UK-PBC risk score.

In another embodiment, elafibranor is administered to a subject with PBC for:
improving AST, γ-GT, 5'-nucleotidase, total bilirubin, conjugated bilirubin, ALT and albumin levels;
improving lipid parameters
improving C4 and/or FGF19 levels
improving IgM levels; and
improving 5D-itch scale, PBC 40 QOL, VAS.

In a particular embodiment, the subject has mild to moderately advanced PBC. For example, the subject can have mild to moderately advanced PBC according to Rotterdam criteria, with no sign of major liver dysfunction as illustrated by bilirubin, albumin or platelet levels within normal ranges.

The invention also relates to elafibranor for use in the improvement of ALP and/or γGT levels in a subject having mild to moderately advanced PBC. In particular, elafibranor is administered for lowering the activity of ALP and/or γGT in a subject having mild to moderately advanced PBC.

In a particular embodiment, elafibranor is administered to a subject with mild to moderately advanced PBC for normalizing ALP, albumin and/or bilirubin level(s).

In a particular embodiment, the subject is with mild to moderately advanced PBC and the treatment results in a level of ALP lower than 1.67×ULN (upper limit of normal) and total bilirubin within normal limit. The reference range of total bilirubin is 0.2-1.2 mg/dL. The reference range of direct bilirubin is 0.1-0.4 mg/dL. In a particular variant of this embodiment, elafibranor is administered for decreasing ALP level by at least 15%.

In another embodiment, the subject is with mild to moderately advanced PBC and the treatment results in a level of ALP lower than 2×ULN (upper limit of normal) and total bilirubin within normal limit. In a particular variant of this embodiment, elafibranor is administered for decreasing ALP level by at least 40%.

In another particular embodiment, the subject is with mild to moderately advanced PBC and the treatment results in a level of ALP lower than 1.5×ULN, total bilirubin within normal limit and a decrease of ALP level greater than 40%.

In a particular embodiment, elafibranor is administered to a subject with mild to moderately advanced PBC, to improve bile acid level such as CDCA, cholic acid, litocholic acid and DCA levels.

In a further embodiment, elafibranor is administered to a subject having mild to moderately advanced PBC for improving Paris I, Paris II, Toronto I, Toronto II or UK-PBC risk score.

In another embodiment, elafibranor is administered to a subject with mild to moderately advanced PBC for:
improving AST, γ-GT, 5'-nucleotidase, total bilirubin, conjugated bilirubin, ALT and albumin levels;
improving lipid parameters
improving C4 and/or FGF19 levels
improving IgM levels; and
improving 5D-itch scale, PBC 40 QOL, VAS.

In a particular embodiment, the patient has mild to moderately advanced PBC and responds at least partly to UDCA. In another embodiment, the patient has mild to moderately advanced PBC and does not respond adequately to UDCA. In a particular embodiment, elafibranor is administered, preferably orally, to a patient with mild to moderately advanced PBC and inadequate response to UDCA, in particular at a dose of elafibranor comprised between 70 and 170 mg, such as a dose comprised between 80 and 120 mg, more particularly at a dose of 80 or 120 mg.

In another particular embodiment, elafibranor is administered in combination with UDCA to a subject with mild to moderately advanced PBC and inadequate response to UDCA acid. In a particular embodiment, elafibranor is administered, preferably orally, in combination to UDCA to a patient with mild to moderately advanced PBC and inadequate response to UDCA, in particular at a dose of elafibranor comprised between 70 and 170 mg, such as a dose comprised between 80 and 120 mg, more particularly at a dose of 80 or 120 mg.

The invention also relates to elafibranor for use in combination with UDCA in the improvement of ALP and/or γGT levels in a subject having mild to moderately advanced PBC, in particular at a dose of elafibranor comprised between 70 and 170 mg, such as a dose comprised between 80 and 120 mg, more particularly at a dose of 80 or 120 mg. In particular, elafibranor is administered in combination with UDCA for lowering the activity of ALP and/or γGT in a subject having mild to moderately advanced PBC.

In a particular embodiment, elafibranor is administered in combination to UDCA to a subject with mild to moderately advanced PBC for normalizing ALP, albumin and/or bilirubin level(s), in particular at a dose of elafibranor comprised between 70 and 170 mg, such as a dose comprised between 80 and 120 mg, more particularly at a dose of 80 or 120 mg.

In a particular embodiment, the subject is with mild to moderately advanced PBC and the treatment results in a level of ALP lower than 1.67×ULN (upper limit of normal) and total bilirubin within normal limit. The reference range of total bilirubin is 0.2-1.2 mg/dL. The reference range of direct bilirubin is 0.1-0.4 mg/dL. In a particular variant of this embodiment, elafibranor is administered in combination with UDCA for decreasing ALP level by at least 15%, in particular at a dose of elafibranor comprised between 70 and 170 mg, such as a dose comprised between 80 and 120 mg, more particularly at a dose of 80 or 120 mg.

In another embodiment, the subject is with mild to moderately advanced PBC and the treatment results in a level of ALP lower than 2×ULN (upper limit of normal) and total bilirubin within normal limit. In a particular variant of this embodiment, elafibranor is administered in combination with UDCA for decreasing ALP level by at least 40%, in particular at a dose of elafibranor comprised between 70 and 170 mg, such as a dose comprised between 80 and 120 mg, more particularly at a dose of 80 or 120 mg.

In another particular embodiment, the subject is with mild to moderately advanced PBC and the treatment results in a level of ALP lower than 1.5×ULN, total bilirubin within normal limit and a decrease of ALP level greater than 40%, wherein the subject is administered with elafibranor in combination to UDCA, in particular at a dose of elafibranor comprised between 70 and 170 mg, such as a dose comprised between 80 and 120 mg, more particularly at a dose of 80 or 120 mg.

In a particular embodiment, elafibranor is administered in combination to UDCA to a subject with mild to moderately advanced PBC, to improve bile acids level such as CDCA, cholic acid, litocholic acid and DCA levels, in particular at a dose of elafibranor comprised between 70 and 170 mg, such as a dose comprised between 80 and 120 mg, more particularly at a dose of 80 or 120 mg.

In a further embodiment, elafibranor is administered in combination to UDCA to a subject having mild to moderately advanced PBC for improving Paris I, Paris II, Toronto I, Toronto II or UK-PBC risk score, in particular at a dose of elafibranor comprised between 70 and 170 mg, such as a dose comprised between 80 and 120 mg, more particularly at a dose of 80 or 120 mg.

In another embodiment, elafibranor is administered in combination to UDCA to a subject with mild to moderately advanced PBC for:
improving AST, γ-GT, 5'-nucleotidase, total bilirubin, conjugated bilirubin, ALT and albumin levels;
improving lipid parameters
improving C4 and/or FGF19 levels
improving IgM levels; and
improving 5D-itch scale, PBC 40 QOL, VAS;
in particular at a dose of elafibranor comprised between 70 and 170 mg, such as a dose comprised between 80 and 120 mg, more particularly at a dose of 80 or 120 mg.

The term "treatment" or "treating" refers to therapy, prevention, or prophylaxis of a cholestatic disease in a subject in need thereof. The treatment involves the administration of elafibranor (such as via the administration of a pharmaceutical composition comprising elafibranor) to a subject (e.g., a patient) having a declared disease to prevent, cure, delay, reverse, or slow down the progression of the disease, improving thereby the condition of patients. A treatment may be also administered to subjects that are either healthy or at risk of developing a cholestatic disease.

The term "subject" refers to a mammal and more particularly a human. The subjects to be treated according to the invention can be appropriately selected on the basis of several criteria associated with cholestatic pathological processes such as previous and/or present drug treatments, associated pathologies, genotype, exposure to risk factors, as well as any other relevant biomarker that can be evaluated by means of any suitable immunological, biochemical, or enzymatic method. The subject to be treated is with PBC, as characterized as follows:
the presence of at least 2 of the following 3 diagnostic factors:
(i) history of elevated ALP levels for at least 6 months prior to Day 0 (randomization visit)
(ii) positive Anti-Mitochondrial Antibodies (AMA) titers (>1/40 on immunofluorescence or M2 positive by enzyme-linked immunosorbent assay (ELISA) or positive PBC-specific antinuclear antibodies
(iii) liver biopsy consistent with PBC
ALP≥1.67× upper limit of normal (ULN)
optionally, taking UDCA for at least 12 months (stable dose for ≥6 months) prior to screening visit.

Elafibranor can have different stable isomeric forms.

Synthesis of elafibranor can for example be carried out as described for compound 29 in WO2004/005233.

Elafibranor can be formulated as pharmaceutically acceptable salts, being slightly- or non-toxic salts obtained from organic or inorganic bases or acids of elafibranor. These salts can be obtained during the final purification step of the compound or by incorporating the salt into the previously purified compound.

The pharmaceutical compositions comprising elafibranor for the treatment of cholestatic diseases can comprise one or several excipients or vehicles, acceptable within a pharmaceutical context (e.g., saline solutions, physiological solutions, isotonic solutions, etc., compatible with pharmaceutical usage and well-known by one of ordinary skill in the art). These compositions can comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc. These compositions can be formulated in the form of injectable suspensions, gels, oils, pills, suppositories, powders, gel caps, capsules, aerosols, etc., eventually by means of galenic forms or devices assuring a prolonged and/or slow release. For this kind of formulation, agents such as cellulose, carbonates or starches can advantageously be used.

Elafibranor may be administered in an efficient amount by using a pharmaceutical composition as above-defined.

Elafibranor can be administered in different ways and in different forms that allow administering said compounds in a therapeutically effective amount. Thus, for example, it can be administered in a systematic way, per os, by parenteral route, by inhalation, or by injection, such as for example intravenously, by intra-muscular route, by subcutaneous route, by transdermal route, by intra-arterial route, etc. Oral administration is the preferential route of administration for pharmaceutical compositions comprising elafibranor for the treatment of a cholestatic disease.

The frequency and/or dose relative to the administration can be adapted by one of ordinary skill in the art, in function of the patient, the pathology, the form of administration, etc. Typically, elafibranor can be administered for the treatment of a cholestatic disease at doses varying between 0.01 mg and 1 g per administration, preferentially from 1 mg to 150 mg per administration, and more preferably from 70 mg to 130 mg. Administration can be performed daily or even several times per day, if necessary. In a particular embodiment, elafibranor is administered once a day. In another particular embodiment, elafibranor is administered once a day at a dose of 80 or 120 mg.

In a particular embodiment, the invention relates to the use of elafibranor for the treatment of a cholestatic disease, in combination with at least one other therapeutically active agent. The other active agent may in particular be selected from other anti-cholestatic agents such as UDCA or OCA. The invention thus also relates to the combination of elafibranor with UDCA or OCA. The invention also relates to the combination of elafibranor with an anti-cholestatic agent. Other anti-cholestatic agents include, without limitation:
apical sodium-codependent bile acid transporter inhibitors (ASBTi);
bile acids;
cathepsin inhibitors;
CCR antagonists;
CD40 inhibitors;
CD80 inhibitors;
Dual NOX (NADPH oxidase) 1&4 inhibitors;
Farnesoid X receptor (FXR) agonists;
Fibroblast Growth Factor (FGF) 19 recombinant;
Fractalkine ligand inhibitors;

ileal sodium bile acid cotransporter inhibitors;
Monoclonal antibodies;
PPAR alpha agonists;
PPAR gamma agonists;
PPAR delta agonists;
PPARalpha/gamma agonists;
PPARalpha/delta agonists;
PPAR gamma/delta agonists; and
PPAR alpha/gamma/delta agonists or PPARpan agonists.

Illustrative apical sodium-codependent bile acid transporter inhibitors include, without limitation, A-4250; volixibat; maralixibat formerly SHP-625; GSK-2330672; elobixibat and CJ-14199.

Illustrative bile acids include, without limitation, obeticholic acid and ursodiol (UDCA).

Illustrative cathepsin inhibitors include, without limitation, VBY-376; VBY-825; VBY-036; VBY-129; VBY-285; Org-219517; LY3000328; RG-7236 and BF/PC-18.

Illustrative CCR antagonists include, without limitation, cenicriviroc (CCR2/5 antagonist); PG-092; RAP-310; INCB-10820; RAP-103; PF-04634817 and CCX-872.

Illustrative CD40 inhibitors include, without limitation, FFp-104; xl-050; DOM-0800; XmAb-5485; KGYY-15; FFP-106; TDI-0028 and ABI-793.

Illustrative CD80 inhibitors include, without limitation, RhuDex; FPT-155; ToleriMab; galiximab; SCH-212394; IGM-001; ASP-2408 and SCH-204698.

Illustrative dual NOX (NADPH oxidase) 1&4 inhibitors include, without limitation, GKT-831 (formerly GKT137831) and GKT-901.

Illustrative Farnesoid X receptor (FXR) agonists include, without limitation, obeticholic acid; GS-9674; LJN-452; EDP-305; AKN-083; INT-767; GNF-5120; LY2562175; INV-33; NTX-023-1; EP-024297; Px-103 and SR-45023.

Illustrative Fibroblast Growth Factor 19 (FGF-19) recombinants include, without limitation, NGM-282.

Illustrative Fractalkine ligand inhibitors include, without limitation, E-6011 and KAN-0440567.

Illustrative ileal sodium bile acid cotransporter inhibitors include, without limitation, A-4250; GSK-2330672; volixibat; CJ-14199 and elobixibat.

Illustrative monoclonal antibodies include, without limitation, bertilimumab; NGM-313; IL-20 targeting mAbs; fresolimumab (antiTGFO) formely GC1008; timolumab formely BTT-1023; namacizumab; omalizumab; ranibizumab; bevacizumab; lebrikizumab; epratuzumab; felvizumab; matuzumab; monalizumab; reslizumab and inebilizumab.

Illustrative PPAR alpha agonists include, without limitation, fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate and SR10171; Illustrative PPAR gamma agonists include, without limitation, Pioglitazone, deuterated pioglitazone, Rosiglitazone, efatutazone, ATx08-001, OMS-405, CHS-131, THR-0921, SER-150-DN, KDT-501, GED-0507-34-Levo, CLC-3001 and ALL-4.

Illustrative PPAR delta agonists include, without limitation, GW501516 (Endurabol or ({4-[({4-methyl-2-[4-(trifluoromethyl)phenyl]-1,3-thiazol-5-yl}methyl)sulfanyl]-2-methylphenoxy}acetic acid)) or MBX8025 (Seladelpar or {2-methyl-4-[5-methyl-2-(4-trifluoromethyl-phenyl)-2H-[1,2,3]triazol-4-ylmethylsylfanyl]-phenoxy}-acetic acid) or GW0742 ([4-[[[2-[3-fluoro-4-(trifluoromethyl)phenyl]-4-methyl-5-thiazolyl]methyl]thio]-2-methyl phenoxy]acetic acid) or L165041 or HPP-593 or NCP-1046.

Illustrative PPAR alpha/gamma agonists (also named glitazars) include, without limitation, Saroglitazar, Aleglitazar, Muraglitazar, Tesaglitazar and DSP-8658.

In addition to elafibranor, illustrative PPAR alpha/delta agonists include, without limitation, T913659.

Illustrative PPAR gamma/delta agonists include, without limitation, linoleic acid (CLA) and T3D-959.

Illustrative PPAR alpha/gamma/delta agonists (or "PPAR-pan agonists") include, without limitation, IVA337, TTA (tetradecylthioacetic acid), Bavachinin, GW4148, GW9135, Bezafibrat, Lobeglitazone, and CS038.

In any embodiment comprising the administration of UDCA described above, a particular dose of UDCA administered to the subject can be comprised between 5 and 25 mg/kg/day; such as between 10 and 20 mg/kg/day, more particularly between 13 and 15 mg/kg/day.

In a further embodiment, the present invention provides methods of treating a cholestatic disease comprising the administration of elafibranor or the combination of the invention, in particular in the form of a pharmaceutical composition containing this compound.

In another embodiment, the present invention also provides a kit for treating a cholestatic disease comprising elafibranor, optionally in combination to another anti-cholestatic agent as described above.

The invention is further described with reference to the following, non-limiting, examples.

EXAMPLES

Example 1: ALP and γGT Dosages

Adult subjects with non-alcoholic steatohepatitis (age 18-75 years) were treated at the dose of 80 mg and 120 mg per day of elafibranor over 52 weeks.

A total of 276 NASH patients were randomized: 92 in the placebo group, 93 in the elafibranor 80 mg group and 91 in the elafibranor 120 mg group. Two patients did not receive the study medication and the remaining 274 patients constitute the ITT (intention to treat) population. 33 patients (12%) dropped out during the study. Final liver biopsies were available in 237 patients (77, 82, and 78 patients in the placebo, elafibranor 80 mg, and elafibranor 120 mg groups respectively).

Patients were followed every 2 months with clinical and laboratory evaluations.

Patients treated with both elafibranor doses (80 mg and 120 mg) improved liver function tests (ALT, γGT and alkaline phosphatase) and lipid parameters (triglycerides, LDL-cholesterol, HDL-cholesterol).

Elafibranor lowered alkaline phosphatase (see FIG. 1) and γ-glutamyl transpeptidase (see FIG. 2) in a dose-dependent manner, showing the interest of elafibranor for the treatment of cholestatic diseases.

Beneficial effects of elafibranor on liver function were consistently observed in all patients treated for 1 to 3 months with 80 mg/day elafibranor. Significant reductions in circulating levels of γGT and ALP were observed and reached up to −29% for γGT and −25% for ALP in elafibranor treated groups compared to placebo. In addition, in insulin-resistant patients, elafibranor treatment induced a significant reduction in ALT (−20% compared to placebo), while the level of aspartate aminotransferase (AST) was unchanged.

In the Phase 2a and 2b program, elafibranor has consistently shown a significant decrease in liver enzymes, notably in ALP. A decrease in ALP levels is recognized as a particularly relevant surrogate marker for the treatment of PBC, and was recently used as the basis for FDA approval of OCA in this indication.

The subjects show a dose-related improvement in their disease as shown by a decrease in ALP and γGT.

Example 2: C4 Dosage

The effect of elafibranor was further tested in relation to parameters more directly related to cholestatic diseases than ALP and γGT levels. Thus, it was explored whether treated subjects show a decrease in plasma total bile acids. The measurement of serum 7α-hydroxy-4-cholesten-3-one (7α-HCO, or 7αC4, or C4) is a method for monitoring the enzymatic activity of hepatic cholesterol 7α-hydroxylase, the rate-limiting and major regulatory enzyme in the synthesis of bile acids. Thus a decrease in C4 level reflects a decrease in total bile acids in the patient.

In NASH patients with high ALP level at baseline, elafibranor was orally administered at a dose of either 80 mg or 120 mg per day over 52 weeks.

A total of 62 NASH patients with high ALP levels were randomized: 23 in the placebo group, 16 in the elafibranor 80 mg group and 23 in the elafibranor 120 mg group.

Bile acids precursor levels were improved in the patients having received both elafibranor doses, in a dose-dependent manner.

Example 3: Clinical Trial for PBC

A multicenter, double-blind, randomized, placebo-controlled, phase 2 study clinical trial is conducted in patients with Primary Biliary Cholangitis and inadequate response to ursodeoxycholic acid to evaluate the efficacy and safety of treatment with elafibranor given orally (80 mg daily and 120 mg daily) for 12 weeks.

Primary Objectives

The primary objective is to compare the effect of daily oral administration of elafibranor 80 mg and 120 mg on changes in serum alkaline phosphatase (ALP) to that of placebo in patients with PBC and inadequate response to ursodeoxycholic acid (UDCA).

Secondary Objectives

The secondary objectives are:
to assess the response to treatment based on composite endpoints:
ALP<1.67× upper limit of normal (ULN) and total bilirubin within normal limit and >15% decrease in ALP
ALP<2×ULN and total bilirubin within normal limit and >40% decrease in ALP
to assess response according to:
Paris I, Paris II, Toronto I, Toronto II, UK-PBC risk score
to assess response based on the percent of patients who normalized ALP
to assess response based on the percent of patients who normalized albumin
to assess response based on the percent of patients who normalized bilirubin
to assess the change from baseline in AST, γGT, 5'-nucleotidase, total bilirubin, conjugated bilirubin, ALT, albumin
to assess the change from baseline in lipid parameters
to assess the change from baseline in bile acids: CDCA, cholic acid, litocholic acid, DCA
to assess the change from baseline in C4, FGF19
to assess the change from baseline in IgM
to assess the change from baseline in:
5D-itch scale
PBC 40 QOL
VAS
to assess the tolerability and safety of elafibranor in patients with PBC
to assess pharmacokinetics (PK) of elafibranor 80 mg and 120 mg and its main metabolite in PBC patients and to explore an exposure-response relationship.

Inclusion Criteria

1. Must have provided written informed consent (IC)
2. Males or females 18 to 75 years of age
3. Definite or probable PBC diagnosis as demonstrated by the presence of at least 2 of the following 3 diagnostic factors:
History of elevated ALP levels for at least 6 months prior to Day 0 (randomization visit)
Positive Anti-Mitochondrial Antibodies (AMA) titers (>1/40 on immunofluorescence or M2 positive by enzyme-linked immunosorbent assay (ELISA) or positive PBC-specific antinuclear antibodies
Liver biopsy consistent with PBC
4. ALP≥1.67× upper limit of normal (ULN)
5. Taking UDCA for at least 12 months (stable dose for ≥6 months) prior to screening visit
6. Contraception: Females participating in this study must be of non-childbearing potential or must be using highly efficient contraception for the full duration of the study and for 1 month after the end of treatment, as described below:
a) Cessation of menses for at least 12 months due to ovarian failure
b) Surgical sterilization such as bilateral oophorectomy, hysterectomy, or medically documented ovarian failure
c) If requested by local IRB regulations and/or National laws, sexual abstinence may be considered adequate (the reliability of sexual abstinence needs to be evaluated in relation to the duration of the clinical trial and the preferred and usual lifestyle of the subject)
d) Using a highly effective non-hormonal method of contraception (bilateral tubal occlusion, vasectomised partner or intra-uterine device)
e) Double contraception with barrier and highly effective hormonal method of contraception (oral, intravaginal or transdermal combined estrogen and progestogen hormonal contraception associated with inhibition of ovulation, oral, injectable or implantable progestogen-only hormonal contraception associated with inhibition of ovulation or intrauterine hormone-releasing system). The hormonal contraception must be started at least one month prior to randomization.
7. Must agree to comply with the trial protocol.

Exclusion Criteria:
1. History or presence of other concomitant liver diseases including:
Hepatitis B or C virus (HCV, HBV) infection
Alcoholic liver disease
Definite autoimmune liver disease or overlap hepatitis
Gilbert's Syndrome (due to interpretability of bilirubin levels)
Known history of alpha-1 antitrypsin deficiency
2. Significant renal disease, including nephritic syndrome, chronic kidney disease (defined as patients with markers of kidney damage or estimated glomerular filtration rate [eGFR] of less than 60 mL/min/1.73 m2).
3. Patients with moderate or severe hepatic impairment (defined as Child-Pugh B/C)

4. Platelet count <150×10 3/microliter
5. Albumin <3.5 g/dL
6. Presence of clinical complications of PBC or clinically significant hepatic decompensation, including:
History of liver transplantation, current placement on a liver transplant list, or current Model for End Stage Liver Disease (MELD) score ≥15
Patients with cirrhosis/portal hypertension and complications (or signs and symptoms of cirrhosis/portal hypertension), including known esophageal varices, poorly controlled or diuretic resistant ascites, history of variceal bleeds or related interventions (e.g., insertion of variceal bands or transjugular intrahepatic portosystemic shunts [TIPS]), and hepatic encephalopathy, history or presence of spontaneous bacterial peritonitis, hepatocellular carcinoma
Hepatorenal syndrome (type I or II) or screening serum creatinine >2 mg/dL (178 μmol/L)
7. Administration of the following medications is prohibited as specified below:
2 months preceding screening and throughout the trial (up to the last study visit): fibrates or obeticholic acid, glitazones
3 months prior to screening and throughout the trial (up to the last study visit): azathioprine, colchicine, cyclosporine, methotrexate, mycophenolate mofetil, pentoxifylline; budesonide and other systemic corticosteroids; and potentially hepatotoxic drugs (including a-methyl-dopa, sodium valproic acid, isoniazide, or nitrofurantoin)
12 months prior to inclusion visit and throughout the trial (up to the last study visit): antibodies or immunotherapy directed against interleukins or other cytokines or chemokines
8. If female: known pregnancy, or has a positive urine pregnancy test (confirmed by a positive serum pregnancy test), or lactating
9. Known history of human immunodeficiency virus (HIV) infection
10. Known hypersensitivity to the investigational product or any of its formulation excipients Randomization Patients who satisfy all eligibility criteria will be randomized in a 1:1:1 ratio to one of the following groups:
Elafibranor 80 mg
Elafibranor 120 mg
Placebo A central randomization system will be used (interactive voice/web response system [IVRS/IWRS]).

Primary Endpoint

The primary endpoint is the relative change in serum ALP from baseline to end of treatment in each elafibranor arm, compared to placebo Secondary Endpoint
Response rate in elafibranor 80 mg and 120 mg and placebo groups with response defined as ALP less than 1.67 times ULN and total bilirubin within normal limits and ALP reduction >15%.
Response rate in elafibranor 80 mg and 120 mg and placebo groups with response defined as ALP less than 2 times ULN and total bilirubin within normal limits and ALP reduction >40%
Response rate according to Paris I, Paris II, Toronto I, Toronto II, UK PBC risk score
Alkaline phosphatase response rates of 10%, 20% and 40% decrease
Response rate in elafibranor 80 mg and 120 mg and placebo groups with response defined as percent of patients with normalized ALP at the end of treatment
Response rate in elafibranor 80 mg and 120 mg and placebo groups with response defined as percent of patients with normalized bilirubin at the end of treatment
Response rate in elafibranor 80 mg and 120 mg and placebo groups with response defined as percent of patients with normalized albumin at the end of treatment
Changes from baseline in:
Gamma-glutamyl transferase (γGT)
Alanine aminotransferase (ALT)
Aspartate aminotransferase (AST)
5'-nucleotidase
Bilirubin (total and conjugated)
Albumin
total cholesterol, LDL-chol, HDL-Chol, Triglycerides
Bile acids: CDCA, cholic acid, litocholic acid, DCA
C4, FGF19
IgM
Quality of Life: PBC 40 QOL
Pruritus: 5-D Pruritus Questionnaire and Visual Analogue Score (VAS)
Biomarkers of inflammation and liver fibrosis: TNF-α, TGF-β, IL-6, CK-18 and lysophosphatidic acid
Plasma concentrations of elafibranor and its main metabolite and exposure-response relationship
Adverse Events (AEs)
Cardiovascular parameters (12-lead ECG, heart rate, blood pressure)
Hematology and safety parameters It is expected that elafibranor induces a significant reduction in serum ALP from baseline to end of treatment, compared to placebo. In addition, it is expected that elafibranor induces significant improvement in at least one of the secondary endpoints.

Example 4: Results of Clinical Trial for PBC

Methods

The study protocol and amendments were reviewed by national authorities and Ethics committees at each investigational centre. The trial was registered on www.clinicaltrials.gov (NCT03124108).

Study Population:

This study included adult patients (age 18 to 75 years) with PBC as demonstrated by the presence of at least 2 of the following three diagnostic factors: i) a history of elevated ALP levels for at least 6 months prior to randomization, ii) positive anti-mitochondrial antibodies (AMA) titer (>1/40 on immunofluorescence or M2 positive by enzyme-linked immunoabsorbant assay) or positive PBC specific anti-nuclear antibodies, iii) liver biopsy consistent with PBC. All patients were treated with UDCA for at least 12 months and were at a stable dose for at least 6 months prior to randomization. At inclusion, patients were required to have ALP levels ≥1.67×ULN (ULN=$10^4$ U/L for females; 129 U/L for males). No minimum baseline pruritus was required for inclusion. The main exclusion criteria were i) other liver diseases including viral hepatitis (HBV and HCV), primary sclerosing cholangitis (PSC), alcoholic liver disease, autoimmune hepatitis or overlap, non-alcoholic steatohepatitis (NASH), or history of alpha 1-antitrypsin deficiency; ii) ALT or AST>5×ULN, total bilirubin >2×ULN, platelet count <150×$10^3$/microliter, albumin <3.5 g/dL; iii) moderate or severe hepatic impairment (Child-Pugh B/C); iv) history of liver transplantation, current placement on a liver transplant list, current Model for End Stage Liver Disease (MELD) score ≥15, signs and symptoms of cirrhosis/portal hypertension including ascites, esophageal varices, history of variceal bleeding, hepatic encephalopathy, history of bacterial peritonitis, hepatocellular carcinoma or hepatorenal syndrome. Excluded medications were defined as follows: fibrates, obeticholic acid and glitazones within 2 months prior to screening, azathioprine, colchicine, cyclosporine, methotrexate, mycophenolate mofetil, pentoxifylline; budesonide and other systemic corticosteroids within 3 months prior to screening, or immunotherapy directed against interleukins or other cytokines or chemokines within from 12 months prior to screening visit.

Study Design

This was a randomized, double-blind, placebo controlled clinical trial with 3 parallel groups. Eligible patients who had signed the informed consent were randomized, using an Interactive Response Technology centralized randomization system, in a 1:1:1 ratio to receive elafibranor-80 mg, elafibranor-120 mg, or placebo once daily for 12 weeks. UDCA treatment was continued throughout the study and maintained thereafter. The randomized treatment allocation was performed by permuted block randomisation. During the study, investigators, patients and study personnel were blinded to the treatment allocation. A total of 45 patients were recruited at 21 investigational centers in the US and Europe between 2 May 2017 and 23 Jul. 2018. Assessment visits occurred at randomization (Day-0), week-2, week-4, week-8 and week-12. An end-of-study visit was planned following a protocol amendment implemented after the study start and was performed in a subset of patients after an off study drug period of 16 to 30 days. At each visit, safety was assessed clinically, and blood samples were collected for measurement of efficacy and safety markers by a central laboratory. ALP, liver enzymes and 5'-nucleotidase levels and safety markers were measured at each visit. The bile acid precursor 7α-hydroxy-4-cholesten-3-one (C4), high sensitivity C-reactive protein (hsCRP), IgM, and other inflammatory markers were measured at randomization (Day-0) and at Week-12. Safety assessment included physical examination, vital signs, arterial pressure, electrocardiogram and clinical laboratory testing with hematology, plasma lipids and renal function markers. Pruritus was evaluated at each visit using a visual analog scale (VAS), PBC40 Quality of Life questionnaire and 5D-itch questionnaire.

Primary and Secondary Efficacy Endpoints:

The primary endpoint was the relative change in serum ALP levels from baseline (Day-0) to end-of-treatment (Week-12). Secondary end-points were the percentages of patients achieving predefined therapeutic responses. Notably two main composite definitions were predefined: i) ALP<1.67×ULN and total bilirubin <ULN and ALP reduction >15%, ii) ALP<2×ULN and Total bilirubin<ULN and ALP reduction >40%. Response rate was also assessed according to ALP reduction >10%, >20% and >40%, Paris I, Paris II, Toronto I and Toronto II criteria. Other secondary end-points included change from baseline in γGT, ALT, AST, 5'-nucleotidase, total and conjugated bilirubin, albumin, IgM, hsCRP and other inflammatory markers, bile acid precursor C4, FGF19 and plasma lipids (total cholesterol, LDL-cholesterol, HDL-cholesterol and triglycerides). Change in symptoms was evaluated using PBC40 Quality of Life questionnaire. Safety: Safety and tolerability assessment included adverse events, laboratory variables, a VAS for pruritus, the 5-D pruritus questionnaire (measuring the degree, duration, direction [improvement or worsening], disability [effect on daily activities], and distribution of itching), electrocardiography, physical examination, and vital signs.

Sample Size and Statistical Analysis

Sample size was estimated assuming a standard deviation for the primary endpoint of 18 in each elafibranor arm and 15 for the placebo arm. Fifteen patients per arm (45 in total) were calculated to achieve at least 80% power to detect, for each dose-placebo comparison, a percentage difference of −20% with alpha risk of 0.05 using a two-sided, two-sample, unequal-variance t-test. The 20% difference was chosen based on the effect of elafibranor on ALP levels in patients with NASH. Efficacy analyses were performed on the modified ITT (mITT) population which was pre-defined as all randomized patients who received at least one dose of treatment, with available baseline value and at least 1 post-baseline value under treatment for the primary endpoint. A perprotocol population excluding patients with major deviations to protocol was used for confirmatory analysis on the primary and key secondary efficacy endpoints. All tests of hypotheses were 2-sided and conducted at the 5% significance level, and all confidence intervals (CIs) were 2-sided at the 95% level. No adjustment for multiplicity was made for the primary and secondary efficacy endpoints. As main analysis, the primary efficacy endpoint was compared between each elafibranor dose and placebo using a non-parametric randomization-based analysis of covariance (ANCOVA) with baseline value as a covariate. A sensitivity analysis was also performed using an ANCOVA model with baseline value as a covariate. For continuous secondary efficacy endpoints, the differences in each dose-placebo comparison was assessed on the relative change from baseline using the same method as for the main analysis of the primary efficacy endpoint, and on the absolute change from baseline using an ANCOVA model with baseline value as a covariate. For secondary efficacy endpoints involving binary outcomes, the differences in proportions were assessed independently for each elafibranor dose-placebo comparison using a Fisher exact test. The safety analyses were performed in the safety population pre-defined as all randomized patients who were administered at least one dose of study medication. All statistical analyses were performed using SAS® (Version 9.3 or higher, SAS Institute Inc., Cary, NC, USA).

Results

Sixty-eight patients from 21 centers in Europe and the US were screened for potential inclusion in the trial. Forty-five were randomized to placebo, elafibranor-80 mg or elafibranor-120 mg groups (1:1:1; 15 patients per group). Demographics and baseline clinical characteristics were generally similar between treatment groups (table 1).

TABLE 1

Demographic and Baseline characteristics of the study population (ITT): Descriptive statistics. Values are number of patients for gender, mean ± (SD) for continuous variables except for hsCRP which is noted as median with [min; max].

|  | Elafibranor 80 mg (N = 15) | Elafibranor 120 mg (N = 15) | Placebo (N = 15) | All (N = 45) |
| --- | --- | --- | --- | --- |
| Gender (M/F) | 1/14 | 0/15 | 1/14 | 2/43 |
| Age, years | 56.5 (8.7) | 60.4 (6.9) | 60.5 (8.6) | 59.1 (8.15) |
| UDCA dose, mg/kg | 14.30 (4.01) | 13.50 (3.05) | 14.80 (2.14) | 14.19 (3.13) |
| ALP, IU/L | 350.6 (152.1) | 263.7 (137.6) | 296.2 (115.5) | 303.5 (137.7) |
| γGT, IU/L | 282.3 (215.7) | 161.8 (139.9) | 229.6 (115.9) | 224.6 (166.7) |
| ALT, IU/L | 57.6 (24.7) | 40.5 (16.9) | 48.5 (22.3) | 48.9 (22.2) |
| AST, IU/L | 54.3 (18.7) | 39.4 (15.3) | 46.7 (15.8) | 46.8 (17.4) |
| Bilirubin mg/dL | 0.577 (0.389) | 0.585 (0.303) | 0.651 (0.259) | 0.605 (0.316) |
| Direct bilirubin mg/dL | 0.320 (0.290) | 0.240 (0.070) | 0.301 (0.122) | 0.288 (0.185) |
| Albumin, g/L | 41.0 (3.3) | 41.3 (2.8) | 42.5 (2.9) | 41.6 (3.0) |
| Platelets, $10^9$/L | 271.7 (68.3) | 234.0 (88.6) | 251.9 (74.6) | 252.6 (77.4) |
| 5'-Nucleotidase, IU/L | 21.2 (16.3) | 14.3 (20.4) | 14.4 (11.6) | 16.6 (16.4) |
| IgM, g/L | 2.95 (1.01) | 3.36 (2.16) | 4.60 (2.70) | 3.64 (2.15) |
| hsCRP*, mg/L | 6.40 [2.4; 29.3] | 3.90 [0.4; 35.0] | 5.30 [0.5; 12.3] | 5.30 [0.4; 35.0] |
| C4, nmol/L | 38.6 (37.6) | 42.5 (29.6) | 34.0 (51.6) | 38.7 (39.8) |

In the ITT population, ninety-six percent of patients were women with PBC diagnosis based on positive anti-mitochondrial antibody test and elevated ALP (one patient had a diagnosis of PBC based on a liver biopsy). The mean age was comparable in all groups: 56.5 years in the elafibranor-80 mg, 60.4 years in the elafibranor-120 mg and 60.5 years in placebo. On average, patients in the elafibranor-80 mg group had a higher baseline level of ALP as compared to other groups. Similarly, baseline γGT and 5'-nucleotidase as well as ALT and AST levels were numerically higher in the elafibranor-80 mg group. In all groups patients had mild to moderately advanced PBC, according to Rotterdam criteria, with no sign of major liver dysfunction as illustrated by bilirubin, albumin or platelet levels within normal ranges. All randomized patients completed the study except for one in the elafibranor 120 mg group who stopped participation after only 1 dosing because of a non-drug related SAE (ischemic stroke). This patient did not have a post-baseline ALP value under treatment and was not included in the mITT population. In each group one patient was not included in the per-protocol data set because of major protocol deviation.

Primary Efficacy Endpoint and Effects on ALP Levels:

The primary efficacy end-point of the trial was met at both the 80 and 120 mg doses of elafibranor (FIG. 4A). As compared to placebo, the relative reduction in ALP levels from day 0 to the end-of-treatment period (week 12) was statistically significant in the two elafibranor-treated groups. The mean relative changes±SD were −48.3±14.8% in the elafibranor-80 mg group, and −40.6±17.4% in the elafibranor-120 mg group compared to +3.2±14.8% in the placebo group. The resulting elafibranor effects vs placebo (Mean±SE [95% CI]) were −52.0±5.2% [−62.5% to −41.5%] (p<0.001) and −43.9±6.0% [−55.7% to 32.1%] (p<0.001) for the elafibranor-80 mg and elafibranor-120 mg arms, respectively. These significant effects on ALP (p<0.001) were confirmed in the per-protocol population and in the sensitivity analysis. Compared to the placebo arm, which exhibited stable levels of ALP throughout the study, ALP declined starting at the first on-treatment visit (week 2) in the two elafibranor groups, and continued to decline at a slower rate until the end of the treatment period. During follow-up, ALP increased in the two elafibranor groups after stopping study drug. Although the ALP at baseline was slightly higher in the elafibranor-80 mg group, the relative changes vs baseline were comparable in the two elafibranor-treated groups (FIGS. 4B and 4C).

Response Rates on ALP Defined Efficacy Targets and Composite Endpoints:

In contrast to placebo-treated patients, almost all individuals exposed to elafibranor experienced a sustained drop in ALP. More than 90% of patients treated with elafibranor 80 mg and 120 mg doses had reductions of ALP≥10% (14/15 and 13/14 respectively) or ALP≥20% (14/15 and 13/14) as compared to only 13.3% (2/15) and 6.7% (1/15), respectively, in the placebo arm (p<0.001) (FIG. 5A). None of the placebo treated patients (0/15) showed ALP reduction ≥40% contrasting with high proportions observed in the elafibranor-treated groups (13/15 or 86.7% in the 80 mg arm and 8/14 or 57.1% in the 120 mg arm). Finally, the proportion of patients with normalized ALP levels at the end of the 12-week treatment period was 13.3% (2/15) in the elafibranor-80 mg and 21.4% (3/14) in the elafibranor-120 mg group, but 0% in the placebo group (FIG. 5A). The efficacy of elafibranor was also demonstrated using the composite endpoints that define the risk of PBC-associated complications including liver transplant or death: Paris I, Paris II, Toronto I or Toronto II and Barcelona criteria. Furthermore, both doses of elafibranor showed significant effects vs. placebo on composite endpoints that are used in pivotal phase 3 trials (FIG. 5B). Significantly more patients achieved the composite endpoint of ALP<1.67 ULN, bilirubin <ULN and >15% ALP reduction in the elafibranor-treated groups (10/15 or 66.7% at 80 mg and 11/14 or 78.6% at 120 mg) vs placebo group (1/15 or 6.7%). Similarly, 53.3% (8/15) in the elafibranor-80 mg group and 35.7% (5/14) in the elafibranor-120 mg group reached the more stringent composite endpoint of ALP<1.5×ULN, bilirubin <ULN and ALP reduction ≥40%, while no patient in the placebo group achieved this endpoint (FIG. 5B).

Investigation of PBC-Related Markers, Inflammatory Markers, Aminotransferases and Plasma Lipids:

γGT level remained stable throughout the treatment period in placebo treated patients (+0.2±26%), while significant reductions were observed in both elafibranor-treated groups (at week-12: −37.1±25.5%; p<0.001 vs placebo with 80 mg and −40.0±24.1%; p<0.01 vs placebo with 120 mg) (Table 2 and FIG. 6). The γGT change over time (FIGS. 6A&C) was similar to the changes in ALP observed in the elafibranor-treated groups (FIGS. 4A&C). Additionally, a reduction of 5′-nucleotidase at both doses of elafibranor vs placebo was observed at week 12 (Table 2; FIG. 6). Finally, significant decreases in the elafibranor-treated groups relative to placebo patients were observed in IgM and inflammatory markers including C-reactive protein (Table 2) and haptoglobin (Table 2). Amino-transferases—ALT and AST—were only moderately elevated at baseline and remained stable throughout the treatment period. At week-12, the change vs baseline value was comparable in the two elafibranor and the placebo treated groups (Table 2). Baseline values of bilirubin, platelets and albumin were all within the range of normal and no significant changes occurred during the study period except for albumin that increased significantly by 1.8 g/dl in the elafibranor-120 mg treated group vs. placebo. As expected, patients had features of PBC-related dyslipidemia, notably high HDL-cholesterol at baseline. As compared to placebo, elafibranor treated groups showed decreases in total cholesterol, LDL-cholesterol and triglycerides (Table 2). Finally, circulating levels of the bile acid precursor C4 were decreased in the elafibranor-treated groups, but not in the placebo group (Table 2). Other bile acids did not show statistically significant changes (data not shown). Circulating levels of FGF19 decreased in all groups without any significant difference between elafibranor treated groups and placebo (Table 2).

TABLE 2

| | Baseline (mean ± SD) | | | End of treatment (mean ± SD) | | | Absolute change (mean ± SD) |
|---|---|---|---|---|---|---|---|
| | Ela-80 mg | Ela-120 mg | Placebo | Ela-80 mg | Ela-120 mg | Placebo | Ela-80 mg |
| γGT (IU/L) | 282.3 (215.7) | 158.5 (144.6) | 229.6 (115.9) | 190.8 (171.2) | 96.6 (90.8) | 230.2 (125.3) | −91.5 (95.3) |
| ALT (IU/L) | 57.6 (24.7) | 40.9 (17.5) | 48.5 (22.3) | 57.1 (60.0) | 48.1 (30.4) | 47.3 (21.9) | −0.5 (57.4) |
| AST (IU/L) | 54.3 (18.7) | 40.1 (15.6) | 46.7 (15.75) | 60.3 (61.5) | 51.2 (27.2) | 42.4 (12.9) | 6.0 (55.3) |
| Bilirubin (mg/dL) | 9.9 (6.7) | 9.7 (5.3) | 11.1 (4.4) | 9.7 (6.3) | 9.2 (5.1) | 11.1 (5.7) | −0.2 (3.4) |
| Direct Bilirubin (mg/dL) | 5.5 (5.0) | 4.0 (1.2) | 5.2 (2.1) | 5.8 (5.3) | 4.0 (1.5) | 5.6 (2.8) | 0.3 (2.2) |
| Albumin (g/L) | 41.0 (3.3) | 41.1 (2.7) | 42.5 (2.9) | 43.2 (3.6) | 43.4 (3.6) | 42.5 (1.8) | 2.2 (2.5) |
| 5′-Nucleotidase (IU/L) | 21.2 (16.3) | 14.2 (21.1) | 14.4 (11.6) | 13.4 (12.9) | 9.6 (11.7) | 13.9 (12.3) | −7.8 (8.3) |
| Cholesterol (mmol/L) | 5.9 (1.5) | 6.0 (1.6) | 5.5 (1.0) | 5.4 (1.3) | 5.6 (1.5) | 5.6 (1.0) | −0.5 (0.7) |
| HDL-Chol (mmol/L) | 1.9 (0.5) | 2.0 (0.6) | 2.0 (0.7) | 1.9 (0.5) | 2.0 (0.6) | 2.0 (0.7) | −0.2 (0.4) |
| LDL-Chol (mmol/L) | 3.4 (1.2) | 3.4 (1.3) | 2.9 (0.9) | 3.0 (1.0) | 3.1 (1.2) | 3.0 (0.7) | −0.4 (0.6) |
| Triglycerides (mmol/L) | 1.22 (0.43) | 1.22 (0.36) | 1.31 (0.56) | 1.06 (0.38) | 0.96 (0.28) | 1.29 (0.65) | −0.16 (0.35) |
| IGM (g/L) | 2.95 (1.0) | 3.50 (2.16) | 4.60 (2.70) | 2.61 (0.86) | 3.03 (1.91) | 4.53 (2.45) | −0.34 (0.58) |
| hsCRP (mg/L) | 7.82 (7.40) | 7.29 (8.88) | 5.15 (3.21) | 3.49 (2.10) | 4.21 (3.46) | 5.41 (3.75) | −4.33 (6.31) |
| Haptoglobin (g/L) | 1.45 (0.64) | 1.29 (0.44) | 1.15 (0.55) | 1.19 (0.42) | 1.04 (0.46) | 1.17 (0.60) | −0.27 (0.43) |
| Fibrinogen (g/L) | 4.86 (1.00) | 4.94 (1.02) | 4.27 (0.69) | 4.00 (1.00) | 4.48 (1.00) | 4.21 (1.04) | −0.87 (0.95) |
| C4 (nmol/L) | 38.6 (37.6) | 42.7 (30.7) | 35.0 (51.6) | 22.3 (18.2) | 32.7 (25.7) | 40.2 (51.2) | −16.3 (27.6) |
| FGF-19 (ng/L) | 91.7 (37.3) | 105.1 (62.3) | 142.2 (123.7) | 70.1 (47.8) | 88.2 (68.3) | 95.1 (77.9) | −21.7 (52.6) |

| | Absolute change (mean ± SD) | | Treatment effect vs placebo (LSmean ± SE; [95% IC]) | | P-value vs placebo | |
|---|---|---|---|---|---|---|
| | Ela-120 mg | Placebo | Ela-80 mg | Ela-120 mg | Ela-80 mg | Ela-120 mg |
| γGT (IU/L) | −61.9 (70.8) | 0.6 (54.4) | −77.7 (22.6) [−123.4; −31.2] | −82.0 (23.2) [−128.8; −35.1] | 0.001 | 0.001 |

TABLE 2-continued

Changes in standard laboratory values and exploratory biomarkers

| | | | | | | |
|---|---|---|---|---|---|---|
| ALT (IU/L) | 7.3 (29.1) | −1.2 (8.6) | 2.6 (14.0) [−25.7; 31.0] | 6.8 (14.2) [−21.9; 35.5] | 0.851 | 0.634 |
| AST (IU/L) | 11.1 (28.00) | −4.3 (8.0) | 10.5 (13.7) [−17.1; 38.1] | 15.3 (13.8) [−12.6; 43.3] | 0.446 | 0.274 |
| Bilirubin (mg/dL) | −0.5 (2.8) | −0.0 (3.6) | −0.4 (1.2) [−2.8; 2.0] | −0.7 (1.2) [−3.1; 1.8] | 0.739 | 0.569 |
| Direct Bilirubin (mg/dL) | −0.1 (0.6) | 0.5 (1.5) | −0.1 (0.6) [−1.3; 1.1] | −0.5 (0.6) [−1.8; 0.7] | 0.848 | 0.409 |
| Albumin (g/L) | 2.3 (2.7) | 0.0 (2.2) | 1.7 (0.9) [0.0; 3.5] | 1.8 (0.9) [0.1; 3.6] | 0.054 | 0.044 |
| 5'-Nucleotidase (IU/L) | −4.6 (13.1) | −0.5 (3.5) | −4.8 (2.5) [−9.8; 0.2] | −4.2 (2.5) [−9.2; 0.8] | 0.058 | 0.097 |
| Cholesterol (mmol/L) | −0.4 (0.6) | 0.0 (0.4) | −0.4 (0.2) [−0.8; −0.0] | −0.3 (0.2) [−0.8; 0.1] | 0.040 | 0.099 |
| HDL-Chol (mmol/L) | 0.1 (0.3) | −0.0 (0.3) | 0.0 (0.1) [−0.3; 0.2] | 0.1 (0.1) [−0.2; 0.3] | 0.830 | 0.635 |
| LDL-Chol (mmol/L) | −0.3 (0.5) | 0.1 (0.3) | −0.3 (0.2) [−0.6; 0.01] | −0.3 (0.2) [−0.6; 0.0] | 0.044 | 0.086 |
| Triglycerides (mmol/L) | −0.25 (0.21) | −0.02 (0.38) | −0.20 (0.11) [−0.40; 0.07] | −0.30 (0.11) [−0.5; −0.02] | 0.172 | 0.032 |
| IGM (g/L) | −0.47 (0.55) | −0.08 (0.72) | −0.50 (0.21) [−0.90; −0.07] | −0.60 (0.21) [−1.00; −0.131] | 0.024 | 0.012 |
| hsCRP (mg/L) | −3.08 (6.29) | 0.26 (2.53) | −2.70 (0.89) [−4.50; −0.90] | −1.90 (0.90) [−3.70; −0.00] | 0.004 | 0.046 |
| Haptoglobin (g/L) | −0.25 (0.11) | 0.03 (0.22) | −0.20 (0.10) [−0.40; −0.00] | −0.20 (0.10) [−0.40; −0.00] | 0.031 | 0.017 |
| Fibrinogen (g/L) | −0.47 (0.60) | −0.07 (1.09) | −0.6 (0.33) [−1.2; 0.1] | −0.1 (0.34) [−0.8; 0.5] | 0.094 | 0.679 |
| C4 (nmol/L) | −10.0 (28.6) | 5.2 (10.8) | −20.4 (7.4) [−35.4; −5.4] | −12.9 (7.56) [−28.2; 2.4] | 0.009 | 0.096 |
| FGF-19 (ng/L) | −17.0 (38.9) | −47.1 (69.6) | 4.70 (16.7) [−29.0; 38.5] | 14.9 (16.7) [−18.9; 48.8] | 0.779 | 0.378 |

CONCLUSION

In a randomized phase 2 trial, a 12-week course of elafibranor significantly reduced levels of ALP and other disease activity markers, compared with placebo, in patients with PBC and inadequate response to ursodeoxycholic acid.

Items

1. A method for the treatment of primary sclerosing cholangitis (PSC), the method comprising administering to a subject having PSC a therapeutically effective amount of a composition comprising elafibranor or a pharmaceutically acceptable salt of elafibranor.

2. The method according to item 1, wherein said composition is formulated in a form selected from the group consisting of an injectable suspension, a gel, an oil, a pill, a tablet, a suppository, a powder, a gel cap, a capsule, an aerosol, and a galenic form or device assuring a prolonged and/or slow release.

3. The method according to item 1, wherein elafibranor is administered at a dose comprised between 70 mg and 130 mg per administration.

4. The method according to item 1, wherein elafibranor is administered at a dose comprised between 70 mg and 130 mg per administration.

5. The method according to item 1, wherein elafibranor is administered at a dose of 80 mg per administration.

6. The method according to item 5, wherein elafibranor is administered orally.

7. The method according to item 1, wherein elafibranor is administered at a dose of 120 mg per administration.

8. The method according to item 7, wherein elafibranor is administered orally.

9. The method according to item 1, wherein a tablet comprising 80 mg of elafibranor is administered orally once daily.

10. The method according to item 1, wherein a tablet comprising 120 mg of elafibranor is administered orally once daily.

11. The method according to item 1, the method comprising further administering to the subject in need thereof another anti-cholestatic agent.

REFERENCES

Ali A, Byrne T, Lindor K (2015) Orphan drugs in development for primary biliary cirrhosis: challenges and progress. *Orphan Drugs: Research and Reviews* 2015: 83-97

Beuers U, Gershwin M E, Gish R G, Invernizzi P, Jones D E, Lindor K, Ma X, Mackay I R, Pares A, Tanaka A, Vierling J M, Poupon R (2015) Changing nomenclature for PBC: from 'cirrhosis' to 'cholangitis'. *Gut* 64: 1671-1672

Boonstra K, Beuers U, Ponsioen C Y (2012) Epidemiology of primary sclerosing cholangitis and primary biliary cirrhosis: a systematic review. *J Hepatol* 56: 1181-1188

Ghonem N S, Assis D N, Boyer J L (2015) *Fibrates and cholestasis. Hepatology* 62: 635-643

Lens S, Leoz M, Nazal L, Bruguera M, Pares A (2014) Bezafibrate normalizes alkaline phosphatase in primary biliary cirrhosis patients with incomplete response to ursodeoxycholic acid. *Liver Int* 34: 197-203

Purohit T, Cappell M S (2015) Primary biliary cirrhosis: Pathophysiology, clinical presentation and therapy. *World J Hepatol* 7: 926-941

Boursier J, Abdelmalek M, Caldwell S, Drenth J, Anstee Q M, Hum D, Hanf R, Roudot A, Megnien S, Staels B, Sanyal A (2016) Elafibranor, an Agonist of the Peroxisome Proliferator-Activated Receptor-alpha and -delta, Induces Resolution of Nonalcoholic Steatohepatitis Without Fibrosis Worsening. *Gastroenterology* 150: 1147-1159 e1145

Reshetnyak V I (2015) Primary biliary cirrhosis: Clinical and laboratory criteria for its diagnosis. *World J Gastroenterol* 21: 7683-7708

Zetterman R (2015) Finding the Patient With Primary Biliary Cirrhosis. *Medscape, News & Perspective* available online on 14 Mar. 2016

The invention claimed is:

1. A method for treating pruritus associated to cholestatic disease in a subject having primary biliary cholangitis (PBC) with pruritus and inadequate response to ursodeoxycholic acid, the method comprising administering to said subject a therapeutically effective amount of a composition comprising elafibranor or a pharmaceutically acceptable salt of elafibranor.

2. The method of claim 1, wherein the composition comprises elafibranor.

3. The method of claim 1, wherein said composition is formulated in a form selected from the group consisting of an injectable suspension, a gel, an oil, a pill, a tablet, a suppository, a powder, a gel cap, a capsule, an aerosol, and a galenic form or device assuring a prolonged and/or slow release.

4. The method of claim 1, wherein elafibranor is administered once a day.

5. The method of claim 1, wherein the administration is oral.

6. The method of claim 1, wherein the administration dose is of 80 mg or 120 mg per administration.

7. The method of claim 1, the method comprising further administering to the subject in need thereof another anticholestatic agent.

8. The method of claim 7, wherein the other anti-cholestatic agent is ursodeoxycholic acid (UDCA).

9. The method according to claim 1, the method comprising administering elafibranor at a dose of 80 mg per administration and ursodeoxycholic acid (UDCA), to the subject in need thereof.

* * * * *